(12) United States Patent
Walczak

(10) Patent No.: US 8,007,813 B2
(45) Date of Patent: Aug. 30, 2011

(54) CD95-FC FUSION PROTEINS

(75) Inventor: Henning Walczak, Heidelberg (DE)

(73) Assignees: Apogenix GmbH, Heidelberg (DE);
Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 1099 days.

(21) Appl. No.: 10/551,004

(22) PCT Filed: Mar. 26, 2004

(86) PCT No.: PCT/EP2004/003239
§ 371 (c)(1), (2), (4) Date: Apr. 12, 2007

(87) PCT Pub. No.: WO2004/085478
PCT Pub. Date: Oct. 7, 2004

(65) Prior Publication Data
US 2007/0269449 A1    Nov. 22, 2007

(30) Foreign Application Priority Data
Mar. 26, 2003  (EP) .................. 03006949

(51) Int. Cl.
A61K 38/16 (2006.01)
A61K 38/17 (2006.01)
C12N 5/10 (2006.01)
C12N 5/22 (2006.01)
C07K 14/705 (2006.01)
C07H 21/04 (2006.01)

(52) U.S. Cl. ............ 424/192.1; 435/69.7; 435/325; 530/350; 536/23.4; 514/21.2; 514/21.3

(58) Field of Classification Search .............. None
See application file for complete search history.

(56) References Cited

U.S. PATENT DOCUMENTS
6,015,559 A    1/2000   Lynch et al.

FOREIGN PATENT DOCUMENTS

| | | |
|---|---|---|
| EP | 0 526 452 | 2/1993 |
| EP | 0 965 637 | 12/1999 |
| EP | 0 992 243 | 4/2000 |
| WO | WO 91/08298 A2 | 6/1991 |
| WO | WO 95/27735 | 10/1995 |
| WO | WO 98/36768 | 8/1998 |
| WO | WO 99/50413 | 10/1999 |
| WO | WO 00/18932 | 4/2000 |
| WO | WO 01/41803 A1 | 6/2001 |
| WO | WO 01/49866 | 7/2001 |
| WO | WO 01/49866 A1 | 7/2001 |
| WO | WO 02/066514 | 8/2002 |
| WO | WO 02/079232 A2 | 10/2002 |
| WO | WO 02/079415 | 10/2002 |
| WO | WO 02/090553 | 11/2002 |
| WO | WO 02/090553 A2 | 11/2002 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Palùet al. (1999). In pursuit of new developments for gene therapy. Journal of Biotechnology. 68:1-13.*
Phillips, A.J. (2001). The challenge of gene therapy and DNA delivery. Journal of Pharmacy and Pharmacology. 53:1169-1174.*
Wang et al. (1999). Rapid analysis of gene expression (RAGE) facilitates universal expression profiling. Nucleic Acds Research. 27(23):4609-4618.*
Kaufman et al. (1999). Transgenic analysis of a 100-kb human B-globulin cluster-containing DNA fragment propagated as a bacterial artificial chromosome. Blood. 94(9):3178-3184.*
Demjen, D et al., "Neutralization of CD95 ligand promotes regeneration and functional recovery after spinal cord injury", *Nat. Med* 10(4):389-395, 2004.
Kim, Yon Su et al., "Targeting the IL-15 Receptor with an Antagonist IL-15 Mutant/Fc 2a Protein Blocks Delayed-Type Hypersensitivity", *J Immunol* 160:5742-5748, 1998.
Martin-Villalba, A. et al., "Therapeutic neutralization of CD95-ligand and TNF attenuates brain damage in stroke", *Cell Death Differ.* 8(7):679-686, 2001.
Smith, CA et al., "CD30 antigen, a marker for Hodgkin's lymphoma, is a receptor whose ligand defines an emerging family cytokines with homology to TNF", *Cell* 73(7):1349-1360, 1993.
Capon, Daniel J. et al., "Designing CD4 immunoadhesins for AIDS therapy", Nature, vol. 337, Feb. 9, 1989, pp. 525-531.
Haak-Frendscho, M. et al., "Inhibition of interferon-y by an interferon-y receptor immunoadhesin", Immunology, 1993 vol. 79, pp. 594-599.

\* cited by examiner

*Primary Examiner* — Christine J Saoud
*Assistant Examiner* — Jon M Lockard
(74) *Attorney, Agent, or Firm* — Perkins Coie LLP; Viola T. Kung

(57) ABSTRACT

The invention relates to fusion proteins comprising at least a first domain and a second domain selected from a constant Fc immunoglobulin domain.

14 Claims, 19 Drawing Sheets

Figure 1

CD95

>sp|P25445|TNR6_HUMAN Tumor necrosis factor receptor superfamily member 6 precursor (FASL receptor) (Apoptosis-mediating surface antigen FAS) (Apo-1 antigen) (CD95) - Homo sapiens (Human).

```
1                                                            60
MLGIWTLLPL VLTSVARLSS KSVNAQVTDI NSKGLELRKT VTTVETQNLE GLHHDGQFCH
61                                                          120
KPCPPGERKA RDCTVNGDEP DCVPCQEGKE YTDKAHFSSK CRRCRLCDEG HGLEVEINCT
121                                                         180
RTQNTKCRCK PNFFCNSTVC EHCDPCTKCE HGIIKECTLT SNTKCKEEGS RSNLGWLCLL
181                                                         240
LLPIPLIVWV KRKEVQKTCR KHRKENQGSH ESPTLNPETV AINLSDVDLS KYITTIAGVM
241                                                         300
TLSQVKGFVR KNGVNEAKID EIKNDNVQDT AEQKVQLLRN WHQLHGKKEA YDTLIKDLKK
301                        335
ANLCTLAEKI QTIILKDITS DSENSNFRNE IQSLV
```

AA 1-16 Signal peptide (potential)
AA 17-173 extracellular domain (potential)
AA 47-83 CRD1
AA 84-127 CRD2
AA 128-166 CRD3
AA 174-190 transmembrane (potential)
AA 191-335 cytoplasmic (potential)

Figure 2

IgG1

>sp|P01857|GC1_HUMAN Ig gamma-1 chain C region - Homo sapiens (Human).

```
1                                                              60
ASTKGPSVFP  LAPSSKSTSG  GTAALGCLVK  DYFPEPVTVS  WNSGALTSGV  HTFPAVLQSS
61                                                            120
GLYSLSSVVT  VPSSSLGTQT  YICNVNHKPS  NTKVDKKVEP  KSCDKTHTCP  PCPAPELLGG
121                                                           180
PSVFLFPPKP  KDTLMISRTP  EVTCVVVDVS  HEDPEVKFNW  YVDGVEVHNA  KTKPREEQYN
181                                                           240
STYRVVSVLT  VLHQDWLNGK  EYKCKVSNKA  LPAPIEKTIS  KAKGQPREPQ  VYTLPPSRDE
241                                                           300
LTKNQVSLTC  LVKGFYPSDI  AVEWESNGQP  ENNYKTTPPV  LDSDGSFFLY  SKLTVDKSRW
301                     330
QQGNVFSCSV  MHEALHNHYT  QKSLSLSPGK
```

AA 99-110 hinge region
AA 111-223 CH2 region
AA 224-330 CH3 region
Variants D239E, L241M

Figure 3A

CD95-Fc (AA 1-173 CD95 and AA 102-330 IgG1)

```
1                                                              60
MLGIWTLLPL VLTSVARLSS KSVNAQVTDI NSKGLELRKT VTTVETQNLE GLHHDGQFCH
61                                                            120
KPCPPGERKA RDCTVNGDEP DCVPCQEGKE YTDKAHFSSK CRRCRLCDEG HGLEVEINCT
121                                                           180
RTQNTKCRCK PNFFCNSTVC EHCDPCTKCE HGIIKECTLT SNTKCKEEGS RSCDKTHTCP
181                                                           240
PCPAPELLGG PSVFLFPPKP KDTLMISRTP EVTCVVVDVS HEDPEVKFNW YVDGVEVHNA
241                                                           300
KTKPREEQYN STYRVVSVLT VLHQDWLNGK EYKCKVSNKA LPAPIEKTIS KAKGQPREPQ
301                                                           360
VYTLPPSREE MTKNQVSLTC LVKGFYPSDI AVEWESNGQP ENNYKTTPPV LDSDGSFFLY
361                              400
SKLTVDKSRW QQGNVFSCSV MHEALHNHYT QKSLSLSPGK
```

Figure 3B

Example of a preferred CD95-Fc fusion protein with an overlapping amino acid:

| CD95 extracellular domain | huIgG1 |
|---|---|
| 131                                                          173 | 99                                          120 |
| PNFFCNSTVC EHCDPCTKCE HGIIKECTLT SNTKCKEEGS RSN | EP KSCDKTHTCP PCPAPELLGG |
| PNFFCNSTVC EHCDPCTKCE HGIIKECTLT SNTKCKEEGS RSCDKTHTCPS PCPAPELLGG | |

Figure 4

3. TRAIL-R1

>sp|O00220|T10A_HUMAN Tumor necrosis factor receptor superfamily member 10A precursor (Death receptor 4) (TNF-related apoptosis-inducing ligand receptor 1) (TRAIL receptor-1) (TRAIL-R1) - Homo sapiens (Human).

```
1                                                                  60
MAPPPARVHL GAFLAVTPNP GSAASGTEAA AATPSKVWGS SAGRIEPRGG GRGALPTSMG
61                                                                120
QHGPSARARA GRAPGPRPAR EASPRLRVHK TFKFVVVGVL LQVVPSSAAT IKLHDQSIGT
121                                                               180
QQWEHSPLGE LCPPGSHRSE HPGACNRCTE GVGYTNASNN LFACLPCTAC KSDEEERSPC
181                                                               240
TTTRNTACQC KPGTFRNDNS AEMCRKCSRG CPRGMVKVKD CTPWSDIECV HKESGNGHNI
241                                                               300
WVILVVTLVV PLLLVAVLIV CCCIGSGCGG DPKCMDRVCF WRLGLLRGPG AEDNAHNEIL
301                                                               360
SNADSLSTFV SEQQMESQEP ADLTGVTVQS PGEAQCLLGP AEAEGSQRRR LLVPANGADP
361                                                               420
TETLMLFFDK FANIVPFDSW DQLMRQLDLT KNEIDVVRAG TAGPGDALYA MLMKWVNKTG
421                                      468
RNASIHTLLD ALERMEERHA KEKIQDLLVD SGKFIYLEDG TGSAVSLE
```

AA 1-23 Signal peptide (potential)
AA 24-239 extracellular domain (potential)
AA 107-145 CRD1
AA 147-188 CRD2
AA 189-229 CRD3
AA 240-262 transmembrane (potential)
AA 263-468 cytoplasmic (potential)

Figure 5

Examples of Trail-R1-Fc fusion proteins with overlapping amino acids:

| Trail R1 extracellular domain | huIgG1 |
|---|---|
| 201                                                         239<br>AEMCRKCSRG CPRGMVKVKD CTPWSDIECV HKESGNGHN | 99                                        120<br>EP KSCDKTHTCP PCPAPELLGG |
| AEMCRKCSRG CPRGMVKVKD CTPWSDIECV HKEP KSCDKTHTCP PCPAPELLGG ||
| 201                                                         239<br>AEMCRKCSRG CPRGMVKVKD CTPWSDIECV HKESGNGHN | 99                                        120<br>EP KSCDKTHTCP PCPAPELLGG |
| AEMCRKCSRG CPRGMVKVKD CTPWSDIECV HKSCDKTHTCP PCPAPELLGG ||
| 201                                                         239<br>AEMCRKCSRG CPRGMVKVKD CTPWSDIECV HKESGNGHN | 99                                        120<br>EP KSCDKTHTCP PCPAPELLGG |
| AEMCRKCSRG CPRGMVKVKD CTPWSDIECV HKESCDKTHTCP PCPAPELLGG ||
| 201                                                         239<br>AEMCRKCSRG CPRGMVKVKD CTPWSDIECV HKESGNGHN | 99                                        120<br>EP KSCDKTHTCP PCPAPELLGG |
| AEMCRKCSRG CPRGMVKVKD CTPWSDIECV HKESGNGHTCP PCPAPELLGG ||

Figure 6

4. TRAIL-R2 (long)

>sp|O14763|T10B_HUMAN Tumor necrosis factor receptor superfamily member 10B precursor (Death receptor 5) (TNF-related apoptosis-inducing ligand receptor 2) (TRAIL receptor-2) (TRAIL-R2) - Homo sapiens (Human).

```
1                                                                  60
MEQRGQNAPA ASGARKRHGP GPREARGARP GPRVPKTLVL VVAAVLLLVS AESALITQQD
61                                                                120
LAPQQRAAPQ QKRSSPSEGL CPPGHHISED GRDCISCKYG QDYSTHWNDL LFCLRCTRCD
121                                                               180
SGEVELSPCT TTRNTVCQCE EGTFREEDSP EMCRKCRTGC PRGMVKVGDC TPWSDIECVH
181                                                               240
KESGTKHSGE APAVEETVTS SPGTPASPCS LSGIIIGVTV AAVVLIVAVF VCKSLLWKKV
241                                                               300
LPYLKGICSG GGGDPERVDR SSQRPGAEDN VLNEIVSILQ PTQVPEQEME VQEPAEPTGV
301                                                               360
NMLSPGESEH LLEPAEAERS QRRRLLVPAN EGDPTETLRQ CFDDFADLVP FDSWEPLMRK
361                                                               420
LGLMDNEIKV AKAEAAGHRD TLYTMLIKWV NKTGRDASVH TLLDALETLG ERLAKQKIED
421             440
HLLSSGKFMY LEGNADSAMS
```

AA 1-55 Signal peptide
AA 56-210 extracellular domain (potential)
AA 57-94 CRD1
AA 97-137 CRD2
AA 138-178 CRD3
AA 192-206 TAPE
AA 211-231 transmembrane (potential)
AA 232-440 cytoplasmic (potential)

Figure 7

Examples of Trail-R2(long)-Fc fusion proteins with overlapping amino acids ("repeat" included):

| Trail R2 (long) extracellular domain | huIgG1 |
|---|---|
| 171                                          210<br>TPWSDIECVH KESGTKHSGE APAVEETVTS SPGTPASPCS | 99                                120<br>EP KSCDKTHTCP PCPAPELLGG |
| TPWSDIECVH KESGTKHSGE APAVEETVTS SPGTPASPCSCDKTHTCP PCPAPELLGG<br>Bevorzugte Ausführung (wie in EP 03006949.6 beschrieben) ||
| 171                                          210<br>TPWSDIECVH KESGTKHSGE APAVEETVTS SPGTPASPCS | 99                                120<br>EP KSCDKTHTCP PCPAPELLGG |
| TPWSDIECVH KESGTKHSGE APAVEETVTS SPGTPASCDKTHTCP PCPAPELLGG ||
| 171                                          210<br>TPWSDIECVH KESGTKHSGE APAVEETVTS SPGTPASPCS | 99                                120<br>EP KSCDKTHTCP PCPAPELLGG |
| TPWSDIECVH KESGTKHSGE APAVEETVTS SPGTPAS KSCDKTHTCP PCPAPELLGG ||
| 171                                          210<br>TPWSDIECVH KESGTKHSGE APAVEETVTS SPGTPASPCS | 99                                120<br>EP KSCDKTHTCP PCPAPELLGG |
| TPWSDIECVH KESGTKHSGE APAVEETVTS SPGT KSCDKTHTCP PCPAPELLGG ||
| 171                                          210<br>TPWSDIECVH KESGTKHSGE APAVEETVTS SPGTPASPCS | 99                                120<br>EP KSCDKTHTCP PCPAPELLGG |
| TPWSDIECVH KESGTKHSGE APAVEETVTS SPGTPASPDKTHTCP PCPAPELLGG ||
| 171                                          210<br>TPWSDIECVH KESGTKHSGE APAVEETVTS SPGTPASPCS | 99                                120<br>EP KSCDKTHTCP PCPAPELLGG |
| TPWSDIECVH KESGTKHSGE APAVEETVTS SPG HTCP PCPAPELLGG ||

Figure 8

Examples of Trail-R2(long)-Fc fusion proteins with overlapping amino acids ("repeat" not included):

| Trail R2 (long) extracellular domain | huIgG1 |
|---|---|
| 171                       191<br>TPWSDIECVH KESGTKHSGE A | 99                    120<br>EP KSCDKTHTCP PCPAPELLGG |
| TPWSDIECVH KESGTKHSGEP KSCDKTHTCP PCPAPELLGG ||
| 171                       191<br>TPWSDIECVH KESGTKHSGE A | 99                    120<br>EP KSCDKTHTCP PCPAPELLGG |
| TPWSDIECVH KESGTKSCDKTHTCP PCPAPELLGG ||
| 171                       191<br>TPWSDIECVH KESGTKHSGE A | 99                    120<br>EP KSCDKTHTCP PCPAPELLGG |
| TPWSDIECVH KESGTKHSCDKTHTCP PCPAPELLGG ||
| 171                       191<br>TPWSDIECVH KESGTKHSGE A | 99                    120<br>EP KSCDKTHTCP PCPAPELLGG |
| TPWSDIECVH KESGTHTCP PCPAPELLGG ||
| 171                       191<br>TPWSDIECVH KESGTKHSGE A | 99                    120<br>EP KSCDKTHTCP PCPAPELLGG |
| TPWSDIECVH KESGTKHTCP PCPAPELLGG ||

Figure 9

5. TRAIL-R2 (short)

>sp|O14763|T10B_HUMAN Tumor necrosis factor receptor superfamily member 10B precursor (Death receptor 5) (TNF-related apoptosis-inducing ligand receptor 2) (TRAIL receptor-2) (TRAIL-R2) - Homo sapiens (Human).

```
1                                                                    60
MEQRGQNAPA ASGARKRHGP GPREARGARP GPRVPKTLVL VVAAVLLLVS AESALITQQD
61                                                                  120
LAPQQRAAPQ QKRSSPSEGL CPPGHHISED GRDCISCKYG QDYSTHWNDL LFCLRCTRCD
121                                                                 180
SGEVELSPCT TTRNTVCQCE EGTFREEDSP EMCRKCRTGC PRGMVKVGDC TPWSDIECVH
181                                                                 240
KESGIIIGVT VAAVVLIVAV FVCKSLLWKK VLPYLKGICS GGGGDPERVD RSSQRPGAED
241                                                                 300
NVLNEIVSIL QPTQVPEQEM EVQEPAEPTG VNMLSPGESE HLLEPAEAER SQRRRLLVPA
301                                                                 360
NEGDPTETLR QCFDDFADLV PFDSWEPLMR KLGLMDNEIK VAKAEAAGHR DTLYTMLIKW
361                                                        411
VNKTGRDASV HTLLDALETL GERLAKQKIE DHLLSSGKFM YLEGNADSAM S
```

AA 1-55 Signal peptide
AA 56-184 extracellular domain (potential)
AA 57-94 CRD1
AA 97-137 CRD2
AA 138-178 CRD3
AA 213-202 transmembrane (potential)
AA 203-411 cytoplasmic (potential)

Figure 10

Examples of Trail-R2(short)-Fc fusion proteins with overlapping amino acids:

| Trail-R2 (short) extracellular domain | huIgG1 |
|---|---|
| 151                                184<br>EMCRKCRTGC PRGMVKVGDC TPWSDIECVH KESG | 99                         120<br>EP KSCDKTHTCP PCPAPELLGG |
| EMCRKCRTGC PRGMVKVGDC TPWSDIECVH KEP KSCDKTHTCP PCPAPELLGG | |
| 151                                184<br>EMCRKCRTGC PRGMVKVGDC TPWSDIECVH KESG | 99                         120<br>EP KSCDKTHTCP PCPAPELLGG |
| EMCRKCRTGC PRGMVKVGDC TPWSDIECVH KSCDKTHTCP PCPAPELLGG | |
| 151                                184<br>EMCRKCRTGC PRGMVKVGDC TPWSDIECVH KESG | 99                         120<br>EP KSCDKTHTCP PCPAPELLGG |
| EMCRKCRTGC PRGMVKVGDC TPWSDIECVH KESCDKTHTCP PCPAPELLGG | |
| 151                                184<br>EMCRKCRTGC PRGMVKVGDC TPWSDIECVH KESG | 99                         120<br>EP KSCDKTHTCP PCPAPELLGG |
| EMCRKCRTGC PRGMVKVGDC TPWSDIECVHTCP PCPAPELLGG | |

Figure 11

6. TRAIL-R3

>sp|O14798|T10C_HUMAN Tumor necrosis factor receptor superfamily member 10C precursor (Decoy receptor 1) (DcR1) (Decoy TRAIL receptor without death domain) (TNF- related apoptosis-inducing ligand receptor 3) (TRAIL receptor-3) (TRAIL-R3) (Trail receptor w

```
1                                                                60
MARIPKTLKF VVVIVAVLLP VLAYSATTAR QEEVPQQTVA PQQQRHSFKG EECPAGSHRS
61                                                               120
EHTGACNPCT EGVDYTNASN NEPSCFPCTV CKSDQKHKSS CTMTRDTVCQ CKEGTFRNEN
121                                                              180
SPEMCRKCSR CPSGEVQVSN CTSWDDIQCV EEFGANATVE TPAAEETMNT SPGTPAPAAE
181                                                              240
ETMNTSPGTP APAAEETMTT SPGTPAPAAE ETMTTSPGTP APAAEETMTT SPGTPASSHY
241            259
LSCTIVGIIV LIVLLIVFV
```

AA 1-23 Signal peptide
AA 24-236 extracellular domain
AA 29-66 CRD1
AA 69-109 CRD2
AA 110-149 CRD3
AA 162-236 5 x 15 AA tandem tape repeats
AA 237-259 removed in mature form (potential)

Figure 12

Examples of Trail-R3-Fc fusion proteins with overlapping amino acids ("repeats" included):

| Trail-R3 extracellular domain | huIgG1 |
|---|---|
| 201                                         236<br>SPGTPAPAAE ETMTTSPGTP APAAEETMTT SPGTPA | 99                           120<br>EP KSCDKTHTCP PCPAPELLGG |
| SPGTPAPAAE ETMTTSPGTP APAAEETMTT SPGTP KSCDKTHTCP PCPAPELLGG | |
| 201                                         236<br>SPGTPAPAAE ETMTTSPGTP APAAEETMTT SPGTPA | 99                           120<br>EP KSCDKTHTCP PCPAPELLGG |
| SPGTPAPAAE ETMTTSPGTP APAAEETMTT SP KSCDKTHTCP PCPAPELLGG | |
| 201                                         236<br>SPGTPAPAAE ETMTTSPGTP APAAEETMTT SPGTPA | 99                           120<br>EP KSCDKTHTCP PCPAPELLGG |
| SPGTPAPAAE ETMTTSPGTP APAAEETMTT SCDKTHTCP PCPAPELLGG | |
| 201                                         236<br>SPGTPAPAAE ETMTTSPGTP APAAEETMTT SPGTPA | 99                           120<br>EP KSCDKTHTCP PCPAPELLGG |
| SPGTPAPAAE ETMTTSPGTP APAAEETMTT SPGHTCP PCPAPELLGG | |
| 201                                         236<br>SPGTPAPAAE ETMTTSPGTP APAAEETMT SPGTPA | 99                           120<br>EP KSCDKHTCP PCPAPELLGG |
| SPGTPAPAAE ETMTTSPGTP APAAEETMTHTCP PCPAPELLGG | |
| 201                                         236<br>SPGTPAPAAE ETMTTSPGTP APAAEETMT SPGTPA | 99                           120<br>EP KSCDKHTCP PCPAPELLGG |
| SPGTPAPAAE ETMTTSPGTP APAAEETMTHTCP PCPAPELLGG | |

Figure 13

Examples of Trail-R3-Fc fusion proteins with overlapping amino acids ("repeats" not included):

| Trail-R3 extracellular domain | huIgG1 |
|---|---|
| 121                                              161<br>SPEMCRKCSR CPSGEVQVSN CTSWDDIQCV EEFGANATVE T | 99                          120<br>EP KSCDKTHTCP PCPAPELLGG |
| SPEMCRKCSR CPSGEVQVSN CTSWDDIQCV EEFGANATVEP KSCDKTHTCP PCPAPELLGG ||
| 121                                              161<br>SPEMCRKCSR CPSGEVQVSN CTSWDDIQCV EEFGANATVE T | 99                          120<br>EP KSCDKTHTCP PCPAPELLGG |
| SPEMCRKCSR CPSGEVQVSN CTSWDDIQCV EEP KSCDKTHTCP PCPAPELLGG ||
| 121                                              161<br>SPEMCRKCSR CPSGEVQVSN CTSWDDIQCV EEFGANATVE T | 99                          120<br>EP KSCDKTHTCP PCPAPELLGG |
| SPEMCRKCSR CPSGEVQVSN CTSWDDIQCV EP KSCDKTHTCP PCPAPELLGG ||
| 121                                              161<br>SPEMCRKCSR CPSGEVQVSN CTSWDDIQCV EEFGANATVE T | 99                          120<br>EP KSCDKTHTCP PCPAPELLGG |
| SPEMCRKCSR CPSGEVQVSN CTSWDDIQCV EEFGANATVE HTCP PCPAPELLGG ||
| 121                                              161<br>SPEMCRKCSR CPSGEVQVSN CTSWDDIQCV EEFGANATVE T | 99                          120<br>EP KSCDKTHTCP PCPAPELLGG |
| SPEMCRKCSR CPSGEVQVSN CTSWDDIQCV EEFGANAHTCP PCPAPELLGG ||

Figure 14

7. TRAIL-R4

>sp|Q9UBN6|T10D_HUMAN Tumor necrosis factor receptor superfamily member 10D precursor (Decoy receptor 2) (DcR2) (TNF-related apoptosis-inducing ligand receptor 4) (TRAIL receptor-4) (TRAIL-R4) (TRAIL receptor with a truncated death domain) - Homo sapiens

```
1                                                                      60
MGLWGQSVPT ASSARAGRYP GARTASGTRP WLLDPKILKF VVFIVAVLLP VRVDSATIPR
61                                                                     120
QDEVPQQTVA PQQQRRSLKE EECPAGSHRS EYTGACNPCT EGVDYTIASN NLPSCLLCTV
121                                                                    180
CKSGQTNKSS CTTTRDTVCQ CEKGSFQDKN SPEMCRTCRT GCPRGMVKVS NCTPRSDIKC
181                                                                    240
KNESAASSTG KTPAAEETVT TILGMLASPY HYLIIIVVLV IILAVVVVGF SCRKKFISYL
241                                                                    300
KGICSGGGGG PERVHRVLFR RRSCPSRVPG AEDNARNETL SNRYLQPTQV SEQEIQGQEL
301                                                                    360
AELTGVTVES PEEPQRLLEQ AEAEGCQRRR LLVPVNDADS ADISTLLDAS ATLEEGHAKE
361                     386
TIQDQLVGSE KLFYEEDEAG SATSCL
```

AA 1-55 signal peptide
AA 56-211 extracellular domain (potential)
AA 58-97 CRD1
AA 98-139 CRD2
AA 140-180 CRD3
AA 212-232 transmembrane (potential)
AA 233-386 cytoplasmic (potential)

Figure 15

Examples of Trail-R4-Fc fusion proteins with overlapping amino acids:

| Trail-R4 extracellular domain | huIgG1 |
|---|---|
| 171                                                  211<br>NCTPRSDIKC KNESAASSTG KTPAAEETVT TILGMLASPY H | 99                              120<br>EP KSCDKTHTCP PCPAPELLGG |
| NCTPRSDIKC KNESAASSTG KTPAAEETVT TILGMLASP KSCDKTHTCP PCPAPELLGG ||
| 171                                                  211<br>NCTPRSDIKC KNESAASSTG KTPAAEETVT TILGMLASPY H | 99                              120<br>EP KSCDKTHTCP PCPAPELLGG |
| NCTPRSDIKC KNESAASSTG KTPAAEETVT TILGMLASCDKTHTCP PCPAPELLGG ||
| 171                                                  211<br>NCTPRSDIKC KNESAASSTG KTPAAEETVT TILGMLASPY H | 99                              120<br>EP KSCDKTHTCP PCPAPELLGG |
| NCTPRSDIKC KNESAASSTG KTPAAEETVT THTCP PCPAPELLGG ||
| 171                                                  211<br>NCTPRSDIKC KNESAASSTG KTPAAEETVT TILGMLASPY H | 99                              120<br>EP KSCDKTHTCP PCPAPELLGG |
| NCTPRSDIKC KNESAASSTG KTPAAEETVT TILGMLASPY HTCP PCPAPELLGG ||

Figure 16

1. TNF-R1

>sp|P19438|TR1A_HUMAN Tumor necrosis factor receptor superfamily member 1A precursor (p60) (TNF-R1) (TNF-RI) (p55) (CD120a) [Contains: Tumor necrosis factor binding protein 1 (TBPI)] - Homo sapiens (Human).

```
1                                                                           60
MGLSTVPDLL LPLVLLELLV GIYPSGVIGL VPHLGDREKR DSVCPQGKYI HPQNNSICCT
61                                                                         120
KCHKGTYLYN DCPGPGQDTD CRECESGSFT ASENHLRHCL SCSKCRKEMG QVEISSCTVD
121                                                                        180
RDTVCGCRKN QYRHYWSENL FQCFNCSLCL NGTVHLSCQE KQNTVCTCHA GFFLRENECV
181                                                                        240
SCSNCKKSLE CTKLCLPQIE NVKGTEDSGT TVLLPLVIFF GLCLLSLLFI GLMYRYQRWK
241                                                                        300
SKLYSIVCGK STPEKEGELE GTTTKPLAPN PSFSPTPGFT PTLGFSPVPS STFTSSSTYT
301                                                                        360
PGDCPNFAAP RREVAPPYQG ADPILATALA SDPIPNPLQK WEDSAHKPQS LDTDDPATLY
361                                                                        420
AVVENVPPLR WKEFVRRLGL SDHEIDRLEL QNGRCLREAQ YSMLATWRRR TPRREATLEL
421                                    455
LGRVLRDMDL LGCLEDIEEA LCGPAALPPA PSLLR
```

AA 1-21 Signal peptide
AA 22-211 extracellular domain (potential)
AA 43-82 CRD1
AA 83-125 CRD2
AA 126-166 CRD3
AA 167-196 CRD4
AA 212-234 transmembrane (potential)
AA 235-455 cytoplasmic (potential)

Figure 17

Examples of TNF-R1-Fc fusion proteins with overlapping amino acids:

| TNF-R1 extracellular domain | huIgG1 |
|---|---|
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKGTEP KSCDKTHTCP PCPAPELLGG | |
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKSCDKTHTCP PCPAPELLGG | |
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKTHTCP PCPAPELLGG | |
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKGTEDSCDKTHTCP PCPAPELLGG | |
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKGTEDKTHTCP PCPAPELLGG | |
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKGTEDSGT THTCP PCPAPELLGG | |
| 171                                        211<br>GFFLRENECV SCSNCKKSLE CTKLCLPQIE NVKGTEDSGT T | 99                          120<br>EP KSCDKTHTCP PCPAPELLGG |
| GFFLRENECV SCSNCKKSLE CTKLCLPQIE NVKGTEDSGTHTCP PCPAPELLGG | |

Figure 18

2. TNF-R2

>sp|P20333|TR1B_HUMAN Tumor necrosis factor receptor superfamily member 1B precursor (Tumor necrosis factor receptor 2) (p80) (TNF-R2) (p75) (CD120b) (Etanercept) [Contains: Tumor necrosis factor binding protein 2 (TBPII)] - Homo sapiens (Human).

```
1                                                                    60
MAPVAVWAAL AVGLELWAAA HALPAQVAFT PYAPEPGSTC RLREYYDQTA QMCCSKCSPG
61                                                                  120
QHAKVFCTKT SDTVCDSCED STYTQLWNWV PECLSCGSRC SSDQVETQAC TREQNRICTC
121                                                                 180
RPGWYCALSK QEGCRLCAPL RKCRPGFGVA RPGTETSDVV CKPCAPGTFS NTTSSTDICR
181                                                                 240
PHQICNVVAI PGNASMDAVC TSTSPTRSMA PGAVHLPQPV STRSQHTQPT PEPSTAPSTS
241                                                                 300
FLLPMGPSPP AEGSTGDFAL PVGLIVGVTA LGLLIIGVVN CVIMTQVKKK PLCLQREAKV
301                                                                 360
PHLPADKARG TQGPEQQHLL ITAPSSSSSS LESSASALDR RAPTRNQPQA PGVEASGAGE
361                                                                 420
ARASTGSSDS SPGGHGTQVN VTCIVNVCSS SDHSSQCSSQ ASSTMGDTDS SPSESPKDEQ
421                                        461
VPFSKEECAF RSQLETPETL LGSTEEKPLP LGVPDAGMKP S
```

AA 1-22 Signal peptide
AA 23-257 extracellular domain (potential)
AA 39-76 CRD1
AA 77-118 CRD2
AA 119-162 CRD3
AA 163-201 CRD4
AA 258-287 transmembrane (potential)
AA 288-461 cytoplasmic (potential)

Figure 19

Examples of TNF-R2-Fc fusion proteins with overlapping amino acids:

| TNF-R2 extracellular domain | huIgG1 |
|---|---|
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSPP AEP KSCDKTHTCP PCPAPELLGG ||
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSPP KSCDKTHTCP PCPAPELLGG ||
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSP KSCDKTHTCP PCPAPELLGG ||
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSPP AEGSCDKTHTCP PCPAPELLGG ||
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSCDKTHTCP PCPAPELLGG ||
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSPP AEGSTGDKTHTCP PCPAPELLGG ||
| 221                                             257<br>STRSQHTQPT PEPSTAPSTS FLLPMGPSPP AEGSTGD | 99                           120<br>EP KSCDKTHTCP PCPAPELLGG |
| STRSQHTQPT PEPSTAPSTS FLLPMGPSPP AEGSTHTCP PCPAPELLGG ||

SEQUENCE LISTING

<160> NUMBER OF SEQ ID NOS: 82

<210> SEQ ID NO 1
<211> LENGTH: 30
<212> TYPE: DNA

```
<213> ORGANISM: Artificial Sequence
<220> FEATURE:
<223> OTHER INFORMATION: Description of Artificial Sequence:  PCR primer
      for the amplification of CD95 cDNA
<220> FEATURE:
<223> OTHER INFORMATION: Sense huCD95-Hind III

<400> SEQUENCE: 1
tataaagctt gccaccatgc tgggcatctg                                   30

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: PCR primer
      for the amplification of CD95 cDNA
<220> FEATURE:
<223> OTHER INFORMATION: Antisense huCD95-BgI II

<400> SEQUENCE: 2
tataagatct ggatccttcc tctttgc                                      27

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:  PCR
      primer for the amplification of IgG1 Fc cDNA
<220> FEATURE:
<223> OTHER INFORMATION: Sense huIgG1Fc-BgIII

<400> SEQUENCE: 3
tataagatct tgtgacaaaa ctcacacatg                                   30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: PCR primer
      for the amplification of IgG1 Fc cDNA
<220> FEATURE:
<223> OTHER INFORMATION: Antisense huIgG1Fc-XhoI

<400> SEQUENCE: 4
tatactcgag tcatttaccc ggagacaggg                                   30

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: PCR primer
      for the changing the Kozak Sequence from GCCACCATGC to
      GCCGCCACCATGG
<220> FEATURE:
<223> OTHER INFORMATION: ShuCD95EC_altKozak

<400> SEQUENCE: 5
tataaagctt gccgccacca tggtgggcat c                                 31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:  PCR
      primer for the changing the Kozak Sequence from GCCACCATGC to
```

```
                         GCCGCCACCATGG
<220> FEATURE:
<223> OTHER INFORMATION: AS698 huIgG1Fc-Xho1

<400> SEQUENCE: 6
tatactcgag tcatttaccc ggagacaggg                                    30

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: primer for
      amplifying cDNA of human IgG1 Fc (partial hinge
      CH3)
<220> FEATURE:
<223> OTHER INFORMATION: Sense_huIgG1

<400> SEQUENCE: 7
ccagggactc ctgcctcttg tgacaaaact cacacatg                           38

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: primer for
      amplifying cDNA of human IgG1 Fc (partial hinge
      CH3)
<220> FEATURE:
<223> OTHER INFORMATION: Antisense_ERIhuIgG1

<400> SEQUENCE: 8
tatagaattc tcatttaccc ggagacaggg                                    30

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: primer
      used to amplify the cDNA of TRAILR2 domain
<220> FEATURE:
<223> OTHER INFORMATION: Sense_HIII_TRAILR2

<400> SEQUENCE: 9
tataaagctt gccgccacca tggaacaacg gggacagaac                         40

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: primer
      used to amplify the cDNA of TRAILR2 domain
<220> FEATURE:
<223> OTHER INFORMATION: Antisense_TRAILR2

<400> SEQUENCE: 10
gtgagttttg tcacaagagg caggagtccc tgg                                33

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: primer for
      PCR used to utlilize fragments for cloning purposes
<220> FEATURE:
<223> OTHER INFORMATION: Sense_HIII_TRAILR2
```

-continued

```
<400> SEQUENCE: 11
tataaagctt gccgccacca tggaacaacg gggacagaac                              40

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:  primer for
      PCR used to utlilize fragments for cloning
      purposes
<220> FEATURE:
<223> OTHER INFORMATION: Antisense_ERIhuIgG1

<400> SEQUENCE: 12
tatagaattc tcatttaccc ggagacaggg                                         30

<210> SEQ ID NO 13
<211> LENGTH: 335
<212> TYPE: PRT
<213> ORGANISM: human
<220> FEATURE:
<223> OTHER INFORMATION: CD95 >sp/P25445/TNR6_HUMAN Tumor necrosis
      factor receptor superfamily 6 precursor (FASL-receptor)
      (Apoptosis-mediating surface antigen FAS) (Apo-1
      antigen) (CD95) - Homo sapiens (Human)

<400> SEQUENCE: 13
```

Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
                 20                  25                  30

Lys Gly Leu Glu Leu Arg Lys Thr Val Thr Thr Val Glu Thr Gln Asn
             35                  40                  45

Leu Glu Gly Leu His His Asp Gly Gln Phe Cys His Lys Pro Cys Pro
         50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
        130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
                180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
        210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu

```
            245                 250                 255
Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
            275                 280                 285

Glu Ala Tyr Asp Thr Leu Ile Lys Asp Leu Lys Lys Ala Asn Leu Cys
            290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 14
<211> LENGTH: 330
<212> TYPE: PRT
<213> ORGANISM: human
<220> FEATURE:
<223> OTHER INFORMATION: IgG1 > sp/P01857/GC1_HUMAN Ig gamma-1 chain C
      region - Homo sapiens (Human)

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 400
<212> TYPE: PRT
<213> ORGANISM: Artificial Sequence
<220> FEATURE:
<221> NAME/KEY: MUTAGEN
<222> LOCATION: (1)..(400)
<223> OTHER INFORMATION: CD95-Fc fusion protein  (AA 1-172 CD95 and AA
      102-330 IgG1)
<220> FEATURE:
<223> OTHER INFORMATION: Description of Artificial Sequence: fusion
      protein

<400> SEQUENCE: 15

Met Leu Gly Ile Trp Thr Leu Leu Pro Leu Val Leu Thr Ser Val Ala
 1               5                  10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
            35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Cys Asp Lys Thr
                165                 170                 175

His Thr Cys Pro Pro Cys Pro Ala Pro Glu Leu Leu Gly Gly Pro Ser
            180                 185                 190

Val Phe Leu Phe Pro Pro Lys Pro Lys Asp Thr Leu Met Ile Ser Arg
    195                 200                 205

Thr Pro Glu Val Thr Cys Val Val Val Asp Val Ser His Glu Asp Pro
210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
    275                 280                 285
```

```
Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
370                 375                 380

Leu His Asn His Tyr Thr Gln Lys Ser Leu Ser Leu Ser Pro Gly Lys
385                 390                 395                 400

<210> SEQ ID NO 16
<211> LENGTH: 43
<212> TYPE: PRT
<213> ORGANISM: human
<220> FEATURE:
<223> OTHER INFORMATION: CD95 extracellular domain  (AA 131-173)

<400> SEQUENCE: 16

Pro Asn Phe Phe Cys Asn Ser Thr Val Cys Glu His Cys Asp Pro Cys
1               5                   10                  15

Thr Lys Cys Glu His Gly Ile Ile Lys Glu Cys Thr Leu Thr Ser Asn
            20                  25                  30

Thr Lys Cys Lys Glu Glu Gly Ser Arg Ser Asn
        35                  40

<210> SEQ ID NO 17
<211> LENGTH: 22
<212> TYPE: PRT
<213> ORGANISM: human
<220> FEATURE:
<223> OTHER INFORMATION: huIgG1 (AA 99-120)

<400> SEQUENCE: 17

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 18
<211> LENGTH: 60
<212> TYPE: PRT
<213> ORGANISM: Artificial Sequence
<220> FEATURE:
<223> OTHER INFORMATION: CD95-Fc fusion protein of CD95 extracellular
      domain (AA 131-173) and huIgG1 (AA99-120) with an
      overlapping amino acid (CD95 AA 172 and huIgG1 AA
      102)
<220> FEATURE:
<223> OTHER INFORMATION: Description of Artificial Sequence:  fusion
      protein

<400> SEQUENCE: 18

Pro Asn Phe Phe Cys Asn Ser Thr Val Cys Glu His Cys Asp Pro Cys
1               5                   10                  15

Thr Lys Cys Glu His Gly Ile Ile Lys Glu Cys Thr Leu Thr Ser Asn
            20                  25                  30

Thr Lys Cys Lys Glu Glu Gly Ser Arg Ser Cys Asp Lys Thr His Thr
```

```
                          35                  40                  45
Cys Pro Pro Cys Pro Ala Pro Glu Leu Leu Gly Gly
         50                  55                  60

<210> SEQ ID NO 19
<211> LENGTH: 468
<212> TYPE: PRT
<213> ORGANISM: human
<220> FEATURE:
<223> OTHER INFORMATION: TRAIL-R1  >sp/O00220/T10A_HUMAN Tumor necrosis
      factor receptor superfamily member 10A precursor
      (Death receptor 4) (TNF-related
      apoptosis-including ligand receptor 1) (TRAIL
      receptor-1) (TRAIL-R1)

<400> SEQUENCE: 19

Met Ala Pro Pro Ala Arg Val His Leu Gly Ala Phe Leu Ala Val
  1               5                  10                  15

Thr Pro Asn Pro Gly Ser Ala Ala Ser Gly Thr Glu Ala Ala Ala
                 20                  25                  30

Thr Pro Ser Lys Val Trp Gly Ser Ala Gly Arg Ile Glu Pro Arg
             35                  40                  45

Gly Gly Gly Arg Gly Ala Leu Pro Thr Ser Met Gly Gln His Gly Pro
         50                  55                  60

Ser Ala Arg Ala Arg Ala Gly Arg Ala Pro Gly Pro Arg Pro Ala Arg
 65                  70                  75                  80

Glu Ala Ser Pro Arg Leu Arg Val His Lys Thr Phe Lys Phe Val Val
                 85                  90                  95

Val Gly Val Leu Leu Gln Val Pro Ser Ala Ala Thr Ile Lys
                100                 105                 110 Lys

Leu His Asp Gln Ser Ile Gly Thr Gln Gln Trp Glu His Ser Pro Leu
                115                 120                 125

Gly Glu Leu Cys Pro Pro Gly Ser His Arg Ser Glu His Pro Gly Ala
            130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
            195                 200                 205

Arg Gly Cys Pro Arg Gly Met Val Lys Val Lys Asp Cys Thr Pro Trp
210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Val Ala
                245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
    275                 280                 285

Pro Gly Ala Glu Asp Asn Ala His Asn Glu Ile Leu Ser Asn Ala Asp
        290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
```

```
                    325                 330                 335

Leu Leu Gly Pro Ala Glu Ala Glu Gly Ser Gln Arg Arg Arg Leu Leu
            340                 345                 350

Val Pro Ala Asn Gly Ala Asp Pro Thr Glu Thr Leu Met Leu Phe Phe
            355                 360                 365

Asp Lys Phe Ala Asn Ile Val Pro Phe Asp Ser Trp Asp Gln Leu Met
            370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Lys Glu Lys Ile Gln Asp Leu Leu
            435                 440                 445

Val Asp Ser Gly Lys Phe Ile Tyr Leu Glu Asp Gly Thr Gly Ser Ala
            450                 455                 460

Val Ser Leu Glu
465

<210> SEQ ID NO 20
<211> LENGTH: 39
<212> TYPE: PRT
<213> ORGANISM: human
<220> FEATURE:
<223> OTHER INFORMATION: Trail R1 extracellular domain (AA 201-239)

<400> SEQUENCE: 20

Ala Glu Met Cys Arg Lys Cys Ser Arg Gly Cys Pro Arg Gly Met Val
1               5                   10                  15

Lys Val Lys Asp Cys Thr Pro Trp Ser Asp Ile Glu Cys Val His Lys
            20                  25                  30

Glu Ser Gly Asn Gly His Asn
        35

<210> SEQ ID NO 21
<211> LENGTH: 54
<212> TYPE: PRT
<213> ORGANISM: Artificial Sequence
<220> FEATURE:
<223> OTHER INFORMATION: Trail-R1-Fc fusion protein of Trail R1
      extracellular domain (AA 201-239) and huIgG1
      (AA99-120) with an overlapping amino acid (TRAILR1
      AA 233 and huIgG1 AA 99)
<220> FEATURE:
<223> OTHER INFORMATION: Description of Artificial Sequence: fusion
      protein

<400> SEQUENCE: 21

Ala Glu Met Cys Arg Lys Cys Ser Arg Gly Cys Pro Arg Gly Met Val
1               5                   10                  15

Lys Val Lys Asp Cys Thr Pro Trp Ser Asp Ile Glu Cys Val His Lys
            20                  25                  30

Glu Pro Lys Ser Cys Asp Lys Thr His Thr Cys Pro Pro Cys Pro Ala
        35                  40                  45

Pro Glu Leu Leu Gly Gly
    50

<210> SEQ ID NO 22
<211> LENGTH: 51
<212> TYPE: PRT
```

```
<213> ORGANISM: Artificial Sequence
<220> FEATURE:
<223> OTHER INFORMATION: Trail-R1-Fc fusion protein of Trail R1
      extracellular domain (AA 201-239) and huIgG1 (AA
      99-120) with an overlapping amino acid (TRAILR1 AA
      232 and huIgG1 AA 101)
<220> FEATURE:
<223> OTHER INFORMATION: Description of Artificial Sequence: fusion
      protein

<400> SEQUENCE: 22

Ala Glu Met Cys Arg Lys Cys Ser Arg Gly Cys Pro Arg Gly Met Val
 1               5                  10                  15

Lys Val Lys Asp Cys Thr Pro Trp Ser Asp Ile Glu Cys Val His Lys
            20                  25                  30

Ser Cys Asp Lys Thr His Thr Cys Pro Pro Cys Pro Ala Pro Glu Leu
        35                  40                  45

Leu Gly Gly
    50

<210> SEQ ID NO 23
<211> LENGTH: 52
<212> TYPE: PRT
<213> ORGANISM: Artificial Sequence
<220> FEATURE:
<223> OTHER INFORMATION: Trail-R1-Fc fusion protein of Trail R1
      extracellular domain (AA 201-239) and huIgG1
      (AA99-120) with an overlapping amino acid (TRAILR1
      AA 234 and huIgG1 AA 102)
<220> FEATURE:
<223> OTHER INFORMATION: Description of Artificial Sequence: fusion
      protein

<400> SEQUENCE: 23

Ala Glu Met Cys Arg Lys Cys Ser Arg Gly Cys Pro Arg Gly Met Val
 1               5                  10                  15

Lys Val Lys Asp Cys Thr Pro Trp Ser Asp Ile Glu Cys Val His Lys
            20                  25                  30

Glu Ser Cys Asp Lys Thr His Thr Cys Pro Pro Cys Pro Ala Pro Glu
        35                  40                  45

Leu Leu Gly Gly
    50

<210> SEQ ID NO 24
<211> LENGTH: 51
<212> TYPE: PRT
<213> ORGANISM: Artificial Sequence
<220> FEATURE:
<223> OTHER INFORMATION: Trail-R1-Fc fusion protein of Trail R1
      extracellular domain (AA 201-239) and huIgG1
      (AA99-120) with an overlapping amino acid (TRAILR1
      AA 238 and huIgG1 AA 107)
<220> FEATURE:
<223> OTHER INFORMATION: Description of Artificial Sequence: fusion
      protein

<400> SEQUENCE: 24

Ala Glu Met Cys Arg Lys Cys Ser Arg Gly Cys Pro Arg Gly Met Val
 1               5                  10                  15

Lys Val Lys Asp Cys Thr Pro Trp Ser Asp Ile Glu Cys Val His Lys
            20                  25                  30

Glu Ser Gly Asn Gly His Thr Cys Pro Pro Cys Pro Ala Pro Glu Leu
        35                  40                  45

Leu Gly Gly
    50
```

```
<210> SEQ ID NO 25
<211> LENGTH: 440
<212> TYPE: PRT
<213> ORGANISM: human
<220> FEATURE:
<223> OTHER INFORMATION: Trail-R2  >sp/014763/T10B_HUMAN Tumor necrosis
      factor receptor superfamily member 10B precursor
      (Death receptor 5) (TNF-related
      apoptosis-including ligand receptor 2) (TRAIL
      receptor-2) (TRAIL-R2)

<400> SEQUENCE: 25
```

Met Glu Gln Arg Gly Gln Asn Ala Pro Ala Ala Ser Gly Ala Arg Lys
  1               5                  10                  15

Arg His Gly Pro Gly Pro Arg Glu Ala Arg Gly Ala Arg Pro Gly Pro
             20                  25                  30

Arg Val Pro Lys Thr Leu Val Leu Val Val Ala Ala Val Leu Leu Leu
         35                  40                  45

Val Ser Ala Glu Ser Ala Leu Ile Thr Gln Gln Asp Leu Ala Pro Gln
     50                  55                  60

Gln Arg Ala Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                 85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

```
Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
                435                 440

<210> SEQ ID NO 26
<211> LENGTH: 40
<212> TYPE: PRT
<213> ORGANISM: human
<220> FEATURE:
<223> OTHER INFORMATION: Trail R2 (long) extracellular domain (AA 171
      -210), "repeat" included

<400> SEQUENCE: 26

Thr Pro Trp Ser Asp Ile Glu Cys Val His Lys Glu Ser Gly Thr Lys
1               5                   10                  15

His Ser Gly Glu Ala Pro Ala Val Glu Glu Thr Val Thr Ser Ser Pro
            20                  25                  30

Gly Thr Pro Ala Ser Pro Cys Ser
        35                  40

<210> SEQ ID NO 27
<211> LENGTH: 58
<212> TYPE: PRT
<213> ORGANISM: Artificial Sequence
<220> FEATURE:
<223> OTHER INFORMATION: Trail-R2(long)-Fc fusion protein of Trail R1
      extracellular domain (AA 171-210)Trail R2 (long)
      extracellular domain (AA 171-210), "repeat"
      included) and huIgG1 (AA99-120) with an
      overlapping amino acid
<220> FEATURE:
<223> OTHER INFORMATION: Trail-R2(long)-Fc fusion protein of Trail R2
      extracellular domain (AA 171-210; "repeat"
      included) and huIgG1 (AA99-120) with an
      overlapping amino acid (TRAIL-R2(long) AA 210 and
      huIgG1 AA 102)
<220> FEATURE:
<223> OTHER INFORMATION: Description of Artificial Sequence: fusion
      protein

<400> SEQUENCE: 27

Thr Pro Trp Ser Asp Ile Glu Cys Val His Lys Glu Ser Gly Thr Lys
1               5                   10                  15

His Ser Gly Glu Ala Pro Ala Val Glu Glu Thr Val Thr Ser Ser Pro
            20                  25                  30

Gly Thr Pro Ala Ser Pro Cys Ser Cys Asp Lys Thr His Thr Cys Pro
        35                  40                  45

Pro Cys Pro Ala Pro Glu Leu Leu Gly Gly
    50                  55

<210> SEQ ID NO 28
<211> LENGTH: 55
<212> TYPE: PRT
<213> ORGANISM: Artificial Sequence
<220> FEATURE:
<223> OTHER INFORMATION: Trail-R2(long)-Fc fusion protein of Trail R2
``` extracellular domain (AA 171-210; "repeat"
included) and huIgG1 (AA99-120) with an
overlapping amino acid (TRAIL-R2(long) AA 207 and
huIgG1 AA 102)
<220> FEATURE:
<223> OTHER INFORMATION: Description of Artificial Sequence: fusion
protein

<400> SEQUENCE: 28

```
Thr Pro Trp Ser Asp Ile Glu Cys Val His Lys Glu Ser Gly Thr Lys
  1               5                  10                  15

His Ser Gly Glu Ala Pro Ala Val Glu Glu Thr Val Thr Ser Ser Pro
             20                  25                  30

Gly Thr Pro Ala Ser Cys Asp Lys Thr His Thr Cys Pro Pro Cys Pro
         35                  40                  45

Ala Pro Glu Leu Leu Gly Gly
     50                  55
```

<210> SEQ ID NO 29
<211> LENGTH: 58
<212> TYPE: PRT
<213> ORGANISM: Artificial Sequence
<220> FEATURE:
<223> OTHER INFORMATION: Trail-R2(long)-Fc fusion protein of Trail R2
extracellular domain (AA 171-210; "repeat"
included) and huIgG1 (AA99-120) with an
overlapping amino acid (TRAIL-R2(long) AA 208 and
huIgG1 AA 100)
<220> FEATURE:
<223> OTHER INFORMATION: Description of Artificial Sequence: fusion
protein

<400> SEQUENCE: 29

```
Thr Pro Trp Ser Asp Ile Glu Cys Val His Lys Glu Ser Gly Thr Lys
  1               5                  10                  15

His Ser Gly Glu Ala Pro Ala Val Glu Glu Thr Val Thr Ser Ser Pro
             20                  25                  30

Gly Thr Pro Ala Ser Pro Lys Ser Cys Asp Lys Thr His Thr Cys Pro
         35                  40                  45

Pro Cys Pro Ala Pro Glu Leu Leu Gly Gly
     50                  55
```

<210> SEQ ID NO 30
<211> LENGTH: 55
<212> TYPE: PRT
<213> ORGANISM: Artificial Sequence
<220> FEATURE:
<223> OTHER INFORMATION: Trail-R2(long)-Fc fusion protein of Trail R2
extracellular domain (AA 171-210; "repeat"
included) and huIgG1 (AA99-120) with an
overlapping amino acid (TRAIL-R2(long) AA 205  and
huIgG1 AA 100)
<220> FEATURE:
<223> OTHER INFORMATION: Description of Artificial Sequence: fusion
protein

<400> SEQUENCE: 30

```
Thr Pro Trp Ser Asp Ile Glu Cys Val His Lys Glu Ser Gly Thr Lys
  1               5                  10                  15

His Ser Gly Glu Ala Pro Ala Val Glu Glu Thr Val Thr Ser Ser Pro
             20                  25                  30

Gly Thr Pro Lys Ser Cys Asp Lys Thr His Thr Cys Pro Pro Cys Pro
         35                  40                  45

Ala Pro Glu Leu Leu Gly Gly
     50                  55
```

<210> SEQ ID NO 31
<211> LENGTH: 56
<212> TYPE: PRT
<213> ORGANISM: Artificial Sequence
<220> FEATURE:
<223> OTHER INFORMATION: Trail-R2(long)-Fc fusion protein of Trail R1
      extracellular domain (AA 171-210; "repeat"
      included) and huIgG1 (AA99-120) with an
      overlapping amino acid (TRAIL-R2(long) AA 209 and
      huIgG1 AA 103)
<220> FEATURE:
<223> OTHER INFORMATION: Description of Artificial Sequence: fusion
      protein

<400> SEQUENCE: 31

Thr Pro Trp Ser Asp Ile Glu Cys Val His Lys Glu Ser Gly Thr Lys
 1               5                  10                  15

His Ser Gly Glu Ala Pro Ala Val Glu Glu Thr Val Thr Ser Ser Pro
                20                  25                  30

Gly Thr Pro Ala Ser Pro Cys Asp Lys Thr His Thr Cys Pro Pro Cys
            35                  40                  45

Pro Ala Pro Glu Leu Leu Gly Gly
        50                  55

<210> SEQ ID NO 32
<211> LENGTH: 48
<212> TYPE: PRT
<213> ORGANISM: Artificial Sequence
<220> FEATURE:
<223> OTHER INFORMATION: Trail-R2(long)-Fc fusion protein of Trail R2
      extracellular domain (AA 171-210; "repeat"
      included) and huIgG1 (AA99-120) with an
      overlapping amino acid (TRAIL-R2(long) AA 204 and
      huIgG1 AA 106)
<220> FEATURE:
<223> OTHER INFORMATION: Description of Artificial Sequence: fusion
      protein

<400> SEQUENCE: 32

Thr Pro Trp Ser Asp Ile Glu Cys Val His Lys Glu Ser Gly Thr Lys
 1               5                  10                  15

His Ser Gly Glu Ala Pro Ala Val Glu Glu Thr Val Thr Ser Ser Pro
                20                  25                  30

Gly Thr His Thr Cys Pro Pro Cys Pro Ala Pro Glu Leu Leu Gly Gly
            35                  40                  45

<210> SEQ ID NO 33
<211> LENGTH: 21
<212> TYPE: PRT
<213> ORGANISM: human
<220> FEATURE:
<223> OTHER INFORMATION: Trail R2 (long) extracellular domain (AA 171-
      191; "repeat" not included)

<400> SEQUENCE: 33

Thr Pro Trp Ser Asp Ile Glu Cys Val His Lys Glu Ser Gly Thr Lys
 1               5                  10                  15

His Ser Gly Glu Ala
                20

<210> SEQ ID NO 34
<211> LENGTH: 41
<212> TYPE: PRT
<213> ORGANISM: Artificial Sequence
<220> FEATURE:
<223> OTHER INFORMATION: Trail-R2(long)-Fc fusion protein of Trail R2
      (long) extracellular domain (AA 171-191; "repeat"

not included) and huIgG1 (AA99-120) with an
overlapping amino acid (TRAIL-R2(long) AA190 and
huIgG1 AA99)
<220> FEATURE:
<223> OTHER INFORMATION: Description of Artificial Sequence: fusion
protein

<400> SEQUENCE: 34

Thr Pro Trp Ser Asp Ile Glu Cys Val His Lys Glu Ser Gly Thr Lys
1               5                   10                  15

His Ser Gly Glu Pro Lys Ser Cys Asp Lys Thr His Thr Cys Pro Pro
            20                  25                  30

Cys Pro Ala Pro Glu Leu Leu Gly Gly
        35                  40

<210> SEQ ID NO 35
<211> LENGTH: 35
<212> TYPE: PRT
<213> ORGANISM: Artificial Sequence
<220> FEATURE:
<223> OTHER INFORMATION: Trail-R2(long)-Fc fusion protein of Trail R2
(long) extracellular domain (AA171-191; "repeat"
not included) and huIgG1 (AA99-120) with an
overlapping amino acid (TRAIL-R2(long) AA186 and
huIgG1 AA101)
<220> FEATURE:
<223> OTHER INFORMATION: Description of Artificial Sequence: fusion
protein

<400> SEQUENCE: 35

Thr Pro Trp Ser Asp Ile Glu Cys Val His Lys Glu Ser Gly Thr Lys
1               5                   10                  15

Ser Cys Asp Lys Thr His Thr Cys Pro Pro Cys Pro Ala Pro Glu Leu
            20                  25                  30

Leu Gly Gly
        35

<210> SEQ ID NO 36
<211> LENGTH: 36
<212> TYPE: PRT
<213> ORGANISM: Artificial Sequence
<220> FEATURE:
<223> OTHER INFORMATION: Trail-R2(long)-Fc fusion protein of Trail R2
(long) extracellular domain (AA171-191; "repeat"
not included) and huIgG1 (AA99-120) with an
overlapping amino acid (TRAIL-R2(long) AA188 and
huIgG1 AA102)
<220> FEATURE:
<223> OTHER INFORMATION: Description of Artificial Sequence: fusion
protein

<400> SEQUENCE: 36

Thr Pro Trp Ser Asp Ile Glu Cys Val His Lys Glu Ser Gly Thr Lys
1               5                   10                  15

His Ser Cys Asp Lys Thr His Thr Cys Pro Pro Cys Pro Ala Pro Glu
            20                  25                  30

Leu Leu Gly Gly
        35

<210> SEQ ID NO 37
<211> LENGTH: 29
<212> TYPE: PRT
<213> ORGANISM: Artificial Sequence
<220> FEATURE:
<223> OTHER INFORMATION: Trail-R2(long)-Fc fusion protein of Trail R2
(long) extracellular domain (AA171-191; "repeat"
not included) and huIgG1 (AA99-120) with an
overlapping amino acid (TRAIL-R2(long) AA185 and

```
              huIgG1 AA106)
<220> FEATURE:
<223> OTHER INFORMATION: Description of Artificial Sequence: fusion
      protein

<400> SEQUENCE: 37

Thr Pro Trp Ser Asp Ile Glu Cys Val His Lys Glu Ser Gly Thr His
1               5                   10                  15

Thr Cys Pro Pro Cys Pro Ala Pro Glu Leu Leu Gly Gly
            20                  25

<210> SEQ ID NO 38
<211> LENGTH: 30
<212> TYPE: PRT
<213> ORGANISM: Artificial Sequence
<220> FEATURE:
<223> OTHER INFORMATION: Trail-R2(long)-Fc fusion protein of Trail R2
      (long) extracellular domain (AA171-191; "repeat"
      not included) and huIgG1 (AA99-120) with an
      overlapping amino acid (TRAIL-R2(long) AA187 and
      huIgG1 AA107)
<220> FEATURE:
<223> OTHER INFORMATION: Description of Artificial Sequence: fusion
      protein

<400> SEQUENCE: 38

Thr Pro Trp Ser Asp Ile Glu Cys Val His Lys Glu Ser Gly Thr Lys
1               5                   10                  15

His Thr Cys Pro Pro Cys Pro Ala Pro Glu Leu Leu Gly Gly
            20                  25                  30

<210> SEQ ID NO 39
<211> LENGTH: 411
<212> TYPE: PRT
<213> ORGANISM: human
<220> FEATURE:
<223> OTHER INFORMATION: Trail-R2 (short) >sp/014763/T10B_HUMAN Tumor
      necrosis factor receptor superfamily 10B precursor
      (Death receptor 5) (TNF-related apoptosis-inducing
      ligand receptor 2) (TRAIL receptor-2) (TRAIL-R2)

<400> SEQUENCE: 39

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
        130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
```

```
                165                 170                 175
Glu Cys Val His Lys Glu Ser Gly Ile Ile Ile Gly Val Thr Val Ala
            180                 185                 190
Ala Val Val Leu Ile Val Ala Val Phe Val Cys Lys Ser Leu Leu Trp
            195                 200                 205
Lys Lys Val Leu Pro Tyr Leu Lys Gly Ile Cys Ser Gly Gly Gly Gly
            210                 215                 220
Asp Pro Glu Arg Val Asp Arg Ser Ser Gln Arg Pro Gly Ala Glu Asp
225                 230                 235                 240
Asn Val Leu Asn Glu Ile Val Ser Ile Leu Gln Pro Thr Gln Val Pro
            245                 250                 255
Glu Gln Glu Met Glu Val Gln Glu Pro Ala Glu Pro Thr Gly Val Asn
            260                 265                 270
Met Leu Ser Pro Gly Glu Ser Glu His Leu Leu Glu Pro Ala Glu Ala
            275                 280                 285
Glu Arg Ser Gln Arg Arg Arg Leu Leu Val Pro Ala Asn Glu Gly Asp
            290                 295                 300
Pro Thr Glu Thr Leu Arg Gln Cys Phe Asp Asp Phe Ala Asp Leu Val
305                 310                 315                 320
Pro Phe Asp Ser Trp Glu Pro Leu Met Arg Lys Leu Gly Leu Met Asp
            325                 330                 335
Asn Glu Ile Lys Val Ala Lys Ala Glu Ala Ala Gly His Arg Asp Thr
            340                 345                 350
Leu Tyr Thr Met Leu Ile Lys Trp Val Asn Lys Thr Gly Arg Asp Ala
            355                 360                 365
Ser Val His Thr Leu Leu Asp Ala Leu Glu Thr Leu Gly Glu Arg Leu
            370                 375                 380
Ala Lys Gln Lys Ile Glu Asp His Leu Leu Ser Ser Gly Lys Phe Met
385                 390                 395                 400
Tyr Leu Glu Gly Asn Ala Asp Ser Ala Met Ser
                    405                 410

<210> SEQ ID NO 40
<211> LENGTH: 34
<212> TYPE: PRT
<213> ORGANISM: human
<220> FEATURE:
<223> OTHER INFORMATION: Trail-R2 (short) extracellular domain (AA 151 -
      AA 184)

<400> SEQUENCE: 40

Glu Met Cys Arg Lys Cys Arg Thr Gly Cys Pro Arg Gly Met Val Lys
  1               5                  10                  15
Val Gly Asp Cys Thr Pro Trp Ser Asp Ile Glu Cys Val His Lys Glu
                20                  25                  30
Ser Gly

<210> SEQ ID NO 41
<211> LENGTH: 53
<212> TYPE: PRT
<213> ORGANISM: Artificial Sequence
<220> FEATURE:
<223> OTHER INFORMATION: Trail-R2(short)-Fc fusion protein of Trail R2
      (short) extracellular domain (AA 151-184) and
      huIgG1 (AA 99-120) with an overlapping amino acid
      (TRAIL-R2(short) AA 182 and huIgG1 AA 99)
<220> FEATURE:
<223> OTHER INFORMATION: Description of Artificial Sequence: fusion
      protein
```

```
<400> SEQUENCE: 41

Glu Met Cys Arg Lys Cys Arg Thr Gly Cys Pro Arg Gly Met Val Lys
1               5                   10                  15

Val Gly Asp Cys Thr Pro Trp Ser Asp Ile Glu Cys Val His Lys Glu
            20                  25                  30

Pro Lys Ser Cys Asp Lys Thr His Thr Cys Pro Pro Cys Pro Ala Pro
        35                  40                  45

Glu Leu Leu Gly Gly
        50

<210> SEQ ID NO 42
<211> LENGTH: 50
<212> TYPE: PRT
<213> ORGANISM: Artificial Sequence
<220> FEATURE:
<223> OTHER INFORMATION: Trail-R2(short)-Fc fusion protein of Trail R2
      (short) extracellular domain (AA 151-184) and
      huIgG1 (AA 99-120) with an overlapping amino acid
      (TRAIL-R2(short) AA 181 and huIgG1 AA 101)
<220> FEATURE:
<223> OTHER INFORMATION: Description of Artificial Sequence: fusion
      protein

<400> SEQUENCE: 42

Glu Met Cys Arg Lys Cys Arg Thr Gly Cys Pro Arg Gly Met Val Lys
1               5                   10                  15

Val Gly Asp Cys Thr Pro Trp Ser Asp Ile Glu Cys Val His Lys Ser
            20                  25                  30

Cys Asp Lys Thr His Thr Cys Pro Pro Cys Pro Ala Pro Glu Leu Leu
        35                  40                  45

Gly Gly
    50

<210> SEQ ID NO 43
<211> LENGTH: 51
<212> TYPE: PRT
<213> ORGANISM: Artificial Sequence
<220> FEATURE:
<223> OTHER INFORMATION: Trail-R2(short)-Fc fusion protein of Trail R2
      (short) extracellular domain (AA 151-184) and
      huIgG1 (AA 99-120) with an overlapping amino acid
      (TRAIL-R2(short) AA 183 and huIgG1 AA 102)
<220> FEATURE:
<223> OTHER INFORMATION: Description of Artificial Sequence: fusion
      protein

<400> SEQUENCE: 43

Glu Met Cys Arg Lys Cys Arg Thr Gly Cys Pro Arg Gly Met Val Lys
1               5                   10                  15

Val Gly Asp Cys Thr Pro Trp Ser Asp Ile Glu Cys Val His Lys Glu
            20                  25                  30

Ser Cys Asp Lys Thr His Thr Cys Pro Pro Cys Pro Ala Pro Glu Leu
        35                  40                  45

Leu Gly Gly
        50

<210> SEQ ID NO 44
<211> LENGTH: 43
<212> TYPE: PRT
<213> ORGANISM: Artificial Sequence
<220> FEATURE:
<223> OTHER INFORMATION: Trail-R2(short)-Fc fusion protein of Trail R2
      (short) extracellular domain (AA 151-184) and
      huIgG1 (AA 99-120) with an overlapping amino acid
      (TRAIL-R2(short) AA 180 and huIgG1 AA 107)
```

<220> FEATURE:
<223> OTHER INFORMATION: Description of Artificial Sequence: fusion
      protein

<400> SEQUENCE: 44

Glu Met Cys Arg Lys Cys Arg Thr Gly Cys Pro Arg Gly Met Val Lys
 1               5                  10                  15

Val Gly Asp Cys Thr Pro Trp Ser Asp Ile Glu Cys Val His Thr Cys
             20                  25                  30

Pro Pro Cys Pro Ala Pro Glu Leu Leu Gly Gly
         35                  40

<210> SEQ ID NO 45
<211> LENGTH: 259
<212> TYPE: PRT
<213> ORGANISM: Artificial Sequence
<220> FEATURE:
<223> OTHER INFORMATION: Trail-R3>sp/014798/T10C_HUMAN Tumor necrosis
      factor receptor superfamily member 10C
      precursor;Decoy receptor 1;DcR1;Decoy TRAIL
      receptor without death domain;TNF-related
      apoptosis inducing ligand r3
<220> FEATURE:
<223> OTHER INFORMATION: Description of Artificial Sequence: fusion
      protein

<400> SEQUENCE: 45

Met Ala Arg Ile Pro Lys Thr Leu Lys Phe Val Val Ile Val Ala
 1               5                  10                  15

Val Leu Leu Pro Val Leu Ala Tyr Ser Ala Thr Thr Ala Arg Gln Glu
             20                  25                  30

Glu Val Pro Gln Gln Thr Val Ala Pro Gln Gln Gln Arg His Ser Phe
         35                  40                  45

Lys Gly Glu Glu Cys Pro Ala Gly Ser His Arg Ser Glu His Thr Gly
     50                  55                  60

Ala Cys Asn Pro Cys Thr Glu Gly Val Asp Tyr Thr Asn Ala Ser Asn
 65                  70                  75                  80

Asn Glu Pro Ser Cys Phe Pro Cys Thr Val Cys Lys Ser Asp Gln Lys
                 85                  90                  95

His Lys Ser Ser Cys Thr Met Thr Arg Asp Thr Val Cys Gln Cys Lys
            100                 105                 110

Glu Gly Thr Phe Arg Asn Glu Asn Ser Pro Glu Met Cys Arg Lys Cys
        115                 120                 125

Ser Arg Cys Pro Ser Gly Glu Val Gln Val Ser Asn Cys Thr Ser Trp
    130                 135                 140

Asp Asp Ile Gln Cys Val Glu Glu Phe Gly Ala Asn Ala Thr Val Glu
145                 150                 155                 160

Thr Pro Ala Ala Glu Glu Thr Met Asn Thr Ser Pro Gly Thr Pro Ala
                165                 170                 175

Pro Ala Ala Glu Glu Thr Met Asn Thr Ser Pro Gly Thr Pro Ala Pro
            180                 185                 190

Ala Ala Glu Glu Thr Met Thr Ser Pro Gly Thr Pro Ala Pro Ala
        195                 200                 205

Ala Glu Glu Thr Met Thr Thr Ser Pro Gly Thr Pro Ala Pro Ala Ala
    210                 215                 220

Glu Glu Thr Met Thr Thr Ser Pro Gly Thr Pro Ala Ser Ser His Tyr
225                 230                 235                 240

Leu Ser Cys Thr Ile Val Gly Ile Ile Val Leu Ile Val Leu Leu Ile
                245                 250                 255

-continued

Val Phe Val

<210> SEQ ID NO 46
<211> LENGTH: 36
<212> TYPE: PRT
<213> ORGANISM: human
<220> FEATURE:
<223> OTHER INFORMATION: Trail-R3 extracellular domain (AA 201-236; "repeats" included)

<400> SEQUENCE: 46

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr Thr Ser Pro
             20                  25                  30

Gly Thr Pro Ala
         35

<210> SEQ ID NO 47
<211> LENGTH: 55
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 201-236; "repeats"
      included) and huIgG1 (AA 99-120) with an
      overlapping amino acid (TRAIL-R3 AA 235 and huIgG1
      AA 100)
<220> FEATURE:
<223> OTHER INFORMATION: Description of Artificial Sequence: fusion
      protein

<400> SEQUENCE: 47

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr Thr Ser Pro
             20                  25                  30

Gly Thr Pro Lys Ser Cys Asp Lys Thr His Thr Cys Pro Pro Cys Pro
         35                  40                  45

Ala Pro Glu Leu Leu Gly Gly
     50                  55

<210> SEQ ID NO 48
<211> LENGTH: 52
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 201-236; "repeats"
      included) and huIgG1 (AA 99-120) with an
      overlapping amino acid (TRAIL-R3 AA 232and huIgG1
      AA 100)
<220> FEATURE:
<223> OTHER INFORMATION: Description of Artificial Sequence: fusion
      protein

<400> SEQUENCE: 48

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr Thr Ser Pro
             20                  25                  30

Lys Ser Cys Asp Lys Thr His Thr Cys Pro Pro Cys Pro Ala Pro Glu
         35                  40                  45

Leu Leu Gly Gly
     50

<210> SEQ ID NO 49
<211> LENGTH: 49
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 201-236; "repeats"
      included) and huIgG1 (AA 99-120) with an
      overlapping amino acid (TRAIL-R3 AA 231 and huIgG1
      AA 102)
<220> FEATURE:
<223> OTHER INFORMATION: Description of Artificial Sequence: fusion
      protein

<400> SEQUENCE: 49

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr Thr Ser Cys
                20                  25                  30

Asp Lys Thr His Thr Cys Pro Pro Cys Pro Ala Pro Glu Leu Leu Gly
        35                  40                  45

Gly

<210> SEQ ID NO 50
<211> LENGTH: 48
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 201-236; "repeats"
      included) and huIgG1 (AA 99-120) with an
      overlapping amino acid (TRAIL-R3 AA 234 and huIgG1
      AA 106)
<220> FEATURE:
<223> OTHER INFORMATION: Description of Artificial Sequence: fusion
      protein

<400> SEQUENCE: 50

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr Thr Ser Pro
                20                  25                  30

Gly Thr His Thr Cys Pro Pro Cys Pro Ala Pro Glu Leu Leu Gly Gly
        35                  40                  45

<210> SEQ ID NO 51
<211> LENGTH: 44
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 201-236; "repeats"
      included) and huIgG1 (AA 99-120) with an
      overlapping amino acid (TRAIL-R3 AA 230 and huIgG1
      AA 106)
<220> FEATURE:
<223> OTHER INFORMATION: Description of Artificial Sequence: fusion
      protein

<400> SEQUENCE: 51

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr Thr His Thr
                20                  25                  30

Cys Pro Pro Cys Pro Ala Pro Glu Leu Leu Gly Gly
        35                  40

```
<210> SEQ ID NO 52
<211> LENGTH: 43
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 201-236; "repeats"
      included) and huIgG1 (AA 99-120) with an
      overlapping amino acid (TRAIL-R3 AA 229 and huIgG1
      AA 106)
<220> FEATURE:
<223> OTHER INFORMATION: Description of Artificial Sequence: fusion
      protein

<400> SEQUENCE: 52

Ser Pro Gly Thr Pro Ala Pro Ala Ala Glu Glu Thr Met Thr Thr Ser
 1               5                  10                  15

Pro Gly Thr Pro Ala Pro Ala Ala Glu Glu Thr Met Thr His Thr Cys
                20                  25                  30

Pro Pro Cys Pro Ala Pro Glu Leu Leu Gly Gly
         35                  40

<210> SEQ ID NO 53
<211> LENGTH: 41
<212> TYPE: PRT
<213> ORGANISM: human
<220> FEATURE:
<223> OTHER INFORMATION: Trail-R3 extracellular domain (AA 121-161,
      "repeats" not included)

<400> SEQUENCE: 53

Ser Pro Glu Met Cys Arg Lys Cys Ser Arg Cys Pro Ser Gly Glu Val
 1               5                  10                  15

Gln Val Ser Asn Cys Thr Ser Trp Asp Asp Ile Gln Cys Val Glu Glu
                20                  25                  30

Phe Gly Ala Asn Ala Thr Val Glu Thr
         35                  40

<210> SEQ ID NO 54
<211> LENGTH: 61
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 121-161; "repeats"not
      included) and huIgG1 (AA 99-120) with an
      overlapping amino acid (TRAIL-R3 AA 160 and
      huIgG1 AA 99)
<220> FEATURE:
<223> OTHER INFORMATION: Description of Artificial Sequence: fusion
      protein

<400> SEQUENCE: 54

Ser Pro Glu Met Cys Arg Lys Cys Ser Arg Cys Pro Ser Gly Glu Val
 1               5                  10                  15

Gln Val Ser Asn Cys Thr Ser Trp Asp Asp Ile Gln Cys Val Glu Glu
                20                  25                  30

Phe Gly Ala Asn Ala Thr Val Glu Pro Lys Ser Cys Asp Lys Thr His
         35                  40                  45

Thr Cys Pro Pro Cys Pro Ala Pro Glu Leu Leu Gly Gly
 50                  55                  60

<210> SEQ ID NO 55
<211> LENGTH: 53
<212> TYPE: PRT
<213> ORGANISM: Artificial Sequence
```

-continued

```
<220> FEATURE:
<223> OTHER INFORMATION: Trail-R3-Fc fusion protein of Trail-R3
      extracellular domain (AA 121-161; "repeats"not
      included) and huIgG1 (AA 99-120) with an
      overlapping amino acid (TRAIL-R3 AA 152  and
      huIgG1 AA 99)
<220> FEATURE:
<223> OTHER INFORMATION: Description of Artificial Sequence: fusion
      protein

<400> SEQUENCE: 55

Ser Pro Glu Met Cys Arg Lys Cys Ser Arg Cys Pro Ser Gly Glu Val
 1               5                  10                  15

Gln Val Ser Asn Cys Thr Ser Trp Asp Asp Ile Gln Cys Val Glu Glu
             20                  25                  30

Pro Lys Ser Cys Asp Lys Thr His Thr Cys Pro Pro Cys Pro Ala Pro
         35                  40                  45

Glu Leu Leu Gly Gly
     50

<210> SEQ ID NO 56
<211> LENGTH: 52
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 121-161; "repeats"not
      included) and huIgG1 (AA 99-120) with an
      overlapping amino acid (TRAIL-R3 AA 151 and huIgG1
      AA 99)
<220> FEATURE:
<223> OTHER INFORMATION: Description of Artificial Sequence: fusion
      protein

<400> SEQUENCE: 56

Ser Pro Glu Met Cys Arg Lys Cys Ser Arg Cys Pro Ser Gly Glu Val
 1               5                  10                  15

Gln Val Ser Asn Cys Thr Ser Trp Asp Asp Ile Gln Cys Val Glu Pro
             20                  25                  30

Lys Ser Cys Asp Lys Thr His Thr Cys Pro Pro Cys Pro Ala Pro Glu
         35                  40                  45

Leu Leu Gly Gly
     50

<210> SEQ ID NO 57
<211> LENGTH: 55
<212> TYPE: PRT
<213> ORGANISM: Artificial Sequence
<220> FEATURE:
<223> OTHER INFORMATION: Trail-R3-Fc fusion protein of Trail-R3
      extracellular domain (AA 121-161; "repeats"not
      included) and huIgG1 (AA 99-120) with an
      overlapping amino acid (TRAIL-R3 AA 161  and
      huIgG1 AA 106)
<220> FEATURE:
<223> OTHER INFORMATION: Description of Artificial Sequence: fusion
      protein

<400> SEQUENCE: 57

Ser Pro Glu Met Cys Arg Lys Cys Ser Arg Cys Pro Ser Gly Glu Val
 1               5                  10                  15

Gln Val Ser Asn Cys Thr Ser Trp Asp Asp Ile Gln Cys Val Glu Glu
             20                  25                  30

Phe Gly Ala Asn Ala Thr Val Glu Thr His Thr Cys Pro Pro Cys Pro
         35                  40                  45

Ala Pro Glu Leu Leu Gly Gly
```

-continued

<210> SEQ ID NO 58
<211> LENGTH: 52
<212> TYPE: PRT
<213> ORGANISM: Artificial Sequence
<220> FEATURE:
<223> OTHER INFORMATION: Trail-R3-Fc fusion protein of Trail-R3
    extracellular domain (AA 121-161; "repeats"not
    included) and huIgG1 (AA 99-120) with an
    overlapping amino acid (TRAIL-R3 AA 158 and
    huIgG1 AA 106)
<220> FEATURE:
<223> OTHER INFORMATION: Description of Artificial Sequence: fusion
    protein

<400> SEQUENCE: 58

Ser Pro Glu Met Cys Arg Lys Cys Ser Arg Cys Pro Ser Gly Glu Val
 1               5                  10                  15

Gln Val Ser Asn Cys Thr Ser Trp Asp Asp Ile Gln Cys Val Glu Glu
            20                  25                  30

Phe Gly Ala Asn Ala Thr His Thr Cys Pro Pro Cys Pro Ala Pro Glu
        35                  40                  45

Leu Leu Gly Gly
    50

<210> SEQ ID NO 59
<211> LENGTH: 386
<212> TYPE: PRT
<213> ORGANISM: human
<220> FEATURE:
<223> OTHER INFORMATION: Trail-R4>sp/Q9UBN6/T10D_HUMAN Tumor necrosis
    factor receptor superfamily member 10D
    precursor;Decoy receptor 2; DcR2; TNF-related
    apoptosis-inducing ligand receptor 4)

<400> SEQUENCE: 59

Met Gly Leu Trp Gly Gln Ser Val Pro Thr Ala Ser Ser Ala Arg Ala
 1               5                  10                  15

Gly Arg Tyr Pro Gly Ala Arg Thr Ala Ser Gly Thr Arg Pro Trp Leu
            20                  25                  30

Leu Asp Pro Lys Ile Leu Lys Phe Val Val Phe Ile Val Ala Val Leu
        35                  40                  45

Leu Pro Val Arg Val Asp Ser Ala Thr Ile Pro Arg Gln Asp Glu Val
    50                  55                  60

Pro Gln Gln Thr Val Ala Pro Gln Gln Arg Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110

Pro Ser Cys Leu Leu Cys Thr Val Cys Lys Ser Gly Gln Thr Asn Lys
        115                 120                 125

Ser Ser Cys Thr Thr Thr Arg Asp Thr Val Cys Gln Cys Glu Lys Gly
    130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr Gly Lys Thr
            180                 185                 190

```
Pro Ala Ala Glu Glu Thr Val Thr Thr Ile Leu Gly Met Leu Ala Ser
        195                 200                 205

Pro Tyr His Tyr Leu Ile Ile Ile Val Val Leu Val Ile Ile Leu Ala
        210                 215                 220

Val Val Val Val Gly Phe Ser Cys Arg Lys Lys Phe Ile Ser Tyr Leu
225                 230                 235                 240

Lys Gly Ile Cys Ser Gly Gly Gly Gly Pro Glu Arg Val His Arg
                245                 250                 255

Val Leu Phe Arg Arg Arg Ser Cys Pro Ser Arg Val Pro Gly Ala Glu
                260                 265                 270

Asp Asn Ala Arg Asn Glu Thr Leu Ser Asn Arg Tyr Leu Gln Pro Thr
            275                 280                 285

Gln Val Ser Glu Gln Glu Ile Gln Gly Gln Glu Leu Ala Glu Leu Thr
        290                 295                 300

Gly Val Thr Val Glu Ser Pro Glu Glu Pro Gln Arg Leu Leu Glu Gln
305                 310                 315                 320

Ala Glu Ala Glu Gly Cys Gln Arg Arg Arg Leu Leu Val Pro Val Asn
                325                 330                 335

Asp Ala Asp Ser Ala Asp Ile Ser Thr Leu Leu Asp Ala Ser Ala Thr
                340                 345                 350

Leu Glu Glu Gly His Ala Lys Glu Thr Ile Gln Asp Gln Leu Val Gly
            355                 360                 365

Ser Glu Lys Leu Phe Tyr Glu Glu Asp Glu Ala Gly Ser Ala Thr Ser
        370                 375                 380

Cys Leu
385

<210> SEQ ID NO 60
<211> LENGTH: 41
<212> TYPE: PRT
<213> ORGANISM: human
<220> FEATURE:
<223> OTHER INFORMATION: Trail-R4 extracellular domain (AA 171-211)

<400> SEQUENCE: 60

Asn Cys Thr Pro Arg Ser Asp Ile Lys Cys Lys Asn Glu Ser Ala Ala
 1               5                  10                  15

Ser Ser Thr Gly Lys Thr Pro Ala Ala Glu Glu Thr Val Thr Thr Ile
                20                  25                  30

Leu Gly Met Leu Ala Ser Pro Tyr His
            35                  40

<210> SEQ ID NO 61
<211> LENGTH: 59
<212> TYPE: PRT
<213> ORGANISM: Artificial Sequence
<220> FEATURE:
<223> OTHER INFORMATION: Trail-R4-Fc fusion protein of Trail-R4
      extracellular domain (AA 171-211) and huIgG1 (AA
      99-120) with an overlapping amino acid (TRAIL-R4
      AA 209  and huIgG1 AA 100)
<220> FEATURE:
<223> OTHER INFORMATION: Description of Artificial Sequence: fusion
      protein

<400> SEQUENCE: 61

Asn Cys Thr Pro Arg Ser Asp Ile Lys Cys Lys Asn Glu Ser Ala Ala
 1               5                  10                  15

Ser Ser Thr Gly Lys Thr Pro Ala Ala Glu Glu Thr Val Thr Thr Ile
                20                  25                  30
```

```
Leu Gly Met Leu Ala Ser Pro Lys Ser Cys Asp Lys Thr His Thr Cys
            35                  40                  45

Pro Pro Cys Pro Ala Pro Glu Leu Leu Gly Gly
        50                  55
```

<210> SEQ ID NO 62
<211> LENGTH: 56
<212> TYPE: PRT
<213> ORGANISM: Artificial Sequence
<220> FEATURE:
<223> OTHER INFORMATION: Trail-R4-Fc fusion protein of Trail-R4
      extracellular domain (AA 171-211) and huIgG1 (AA
      99-120) with an overlapping amino acid (TRAIL-R4
      AA 208  and huIgG1 AA 102)
<220> FEATURE:
<223> OTHER INFORMATION: Description of Artificial Sequence: fusion
      protein

<400> SEQUENCE: 62

```
Asn Cys Thr Pro Arg Ser Asp Ile Lys Cys Lys Asn Glu Ser Ala Ala
 1               5                  10                  15

Ser Ser Thr Gly Lys Thr Pro Ala Ala Glu Glu Thr Val Thr Thr Ile
                20                  25                  30

Leu Gly Met Leu Ala Ser Cys Asp Lys Thr His Thr Cys Pro Pro Cys
            35                  40                  45

Pro Ala Pro Glu Leu Leu Gly Gly
        50                  55
```

<210> SEQ ID NO 63
<211> LENGTH: 45
<212> TYPE: PRT
<213> ORGANISM: Artificial Sequence
<220> FEATURE:
<223> OTHER INFORMATION: Trail-R4-Fc fusion protein of Trail-R4
      extracellular domain (AA 171-211) and huIgG1 (AA
      99-120) with an overlapping amino acid (TRAIL-R4
      AA 201  and huIgG1 AA 106)
<220> FEATURE:
<223> OTHER INFORMATION: Description of Artificial Sequence: fusion
      protein

<400> SEQUENCE: 63

```
Asn Cys Thr Pro Arg Ser Asp Ile Lys Cys Lys Asn Glu Ser Ala Ala
 1               5                  10                  15

Ser Ser Thr Gly Lys Thr Pro Ala Ala Glu Glu Thr Val Thr Thr His
                20                  25                  30

Thr Cys Pro Pro Cys Pro Ala Pro Glu Leu Leu Gly Gly
            35                  40                  45
```

<210> SEQ ID NO 64
<211> LENGTH: 54
<212> TYPE: PRT
<213> ORGANISM: Artificial Sequence
<220> FEATURE:
<223> OTHER INFORMATION: Trail-R4-Fc fusion protein of Trail-R4
      extracellular domain (AA 171-211) and huIgG1 (AA
      99-120) with an overlapping amino acid (TRAIL-R4
      AA 211 and huIgG1 AA 107)
<220> FEATURE:
<223> OTHER INFORMATION: Description of Artificial Sequence: fusion
      protein

<400> SEQUENCE: 64

```
Asn Cys Thr Pro Arg Ser Asp Ile Lys Cys Lys Asn Glu Ser Ala Ala
 1               5                  10                  15

Ser Ser Thr Gly Lys Thr Pro Ala Ala Glu Glu Thr Val Thr Thr Ile
                20                  25                  30
```

```
Leu Gly Met Leu Ala Ser Pro Tyr His Thr Cys Pro Pro Cys Pro Ala
        35                  40                  45

Pro Glu Leu Leu Gly Gly
    50

<210> SEQ ID NO 65
<211> LENGTH: 455
<212> TYPE: PRT
<213> ORGANISM: human
<220> FEATURE:
<223> OTHER INFORMATION: TNF-R1 >sp/P19438/TR1A_HUMAN necrosis factor
      receptor superfamily member 1A precursor (p60)
      (TNF-R1) (p55) (CD120a) [contains: Tumor necrosis
      factor binding protein 1 (TBPI)]

<400> SEQUENCE: 65

Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320
```

```
Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
            450                 455

<210> SEQ ID NO 66
<211> LENGTH: 41
<212> TYPE: PRT
<213> ORGANISM: human
<220> FEATURE:
<223> OTHER INFORMATION: TNF-R1 extracellular domain (AA 171-211)

<400> SEQUENCE: 66

Gly Phe Phe Leu Arg Glu Asn Glu Cys Val Ser Cys Ser Asn Cys Lys
1               5                   10                  15

Lys Ser Leu Glu Cys Thr Lys Leu Cys Leu Pro Gln Ile Glu Asn Val
            20                  25                  30

Lys Gly Thr Glu Asp Ser Gly Thr Thr
        35                  40

<210> SEQ ID NO 67
<211> LENGTH: 57
<212> TYPE: PRT
<213> ORGANISM: Artificial Sequence
<220> FEATURE:
<223> OTHER INFORMATION: TNF-R1-Fc fusion protein of TNF-R1
      extracellular domain (AA 171-211) and huIgG1 (AA 99-120) with an
      overlapping amino acid (TNF-R1 AA 206 and huIgG1 AA 99)
<220> FEATURE:
<223> OTHER INFORMATION: Description of Artificial Sequence: fusion
      protein

<400> SEQUENCE: 67

Gly Phe Phe Leu Arg Glu Asn Glu Cys Val Ser Cys Ser Asn Cys Lys
1               5                   10                  15

Lys Ser Leu Glu Cys Thr Lys Leu Cys Leu Pro Gln Ile Glu Asn Val
            20                  25                  30

Lys Gly Thr Glu Pro Lys Ser Cys Asp Lys Thr His Thr Cys Pro Pro
            35                  40                  45

Cys Pro Ala Pro Glu Leu Leu Gly Gly
        50                  55

<210> SEQ ID NO 68
<211> LENGTH: 52
<212> TYPE: PRT
<213> ORGANISM: Artificial Sequence
<220> FEATURE:
<223> OTHER INFORMATION: TNF-R1-Fc fusion protein of TNF-R1
```

```
          extracellular domain (AA 171-211) and huIgG1 (AA 99-120) with an
          overlapping amino acid (TNF-R1 AA 203 and huIgG1 AA 101)
<220> FEATURE:
<223> OTHER INFORMATION: Description of Artificial Sequence:  fusion
      protein

<400> SEQUENCE: 68

Gly Phe Phe Leu Arg Glu Asn Glu Cys Val Ser Cys Ser Asn Cys Lys
 1               5                  10                  15

Lys Ser Leu Glu Cys Thr Lys Leu Cys Leu Pro Gln Ile Glu Asn Val
            20                  25                  30

Lys Ser Cys Asp Lys Thr His Thr Cys Pro Pro Cys Pro Ala Pro Glu
        35                  40                  45

Leu Leu Gly Gly
        50

<210> SEQ ID NO 69
<211> LENGTH: 48
<212> TYPE: PRT
<213> ORGANISM: Artificial Sequence
<220> FEATURE:
<223> OTHER INFORMATION: TNF-R1-Fc fusion protein of TNF-R1
      extracellular domain (AA 171-211) and huIgG1 (AA 99-120) with an
      overlapping amino acid (TNF-R1 AA 203 and huIgG1 AA 105)
<220> FEATURE:
<223> OTHER INFORMATION: Description of Artificial Sequence:  fusion
      protein

<400> SEQUENCE: 69

Gly Phe Phe Leu Arg Glu Asn Glu Cys Val Ser Cys Ser Asn Cys Lys
 1               5                  10                  15

Lys Ser Leu Glu Cys Thr Lys Leu Cys Leu Pro Gln Ile Glu Asn Val
            20                  25                  30

Lys Thr His Thr Cys Pro Pro Cys Pro Ala Pro Glu Leu Leu Gly Gly
        35                  40                  45

<210> SEQ ID NO 70
<211> LENGTH: 56
<212> TYPE: PRT
<213> ORGANISM: Artificial Sequence
<220> FEATURE:
<223> OTHER INFORMATION: TNF-R1-Fc fusion protein of TNF-R1
      extracellular domain (AA 171-211) and huIgG1 (AA 99-120) with an
      overlapping amino acid (TNF-R1 AA 208 and huIgG1 AA 102)
<220> FEATURE:
<223> OTHER INFORMATION: Description of Artificial Sequence:  fusion
      protein

<400> SEQUENCE: 70

Gly Phe Phe Leu Arg Glu Asn Glu Cys Val Ser Cys Ser Asn Cys Lys
 1               5                  10                  15

Lys Ser Leu Glu Cys Thr Lys Leu Cys Leu Pro Gln Ile Glu Asn Val
            20                  25                  30

Lys Gly Thr Glu Asp Ser Cys Asp Lys Thr His Thr Cys Pro Pro Cys
        35                  40                  45

Pro Ala Pro Glu Leu Leu Gly Gly
        50                  55

<210> SEQ ID NO 71
<211> LENGTH: 53
<212> TYPE: PRT
<213> ORGANISM: Artificial Sequence
<220> FEATURE:
<223> OTHER INFORMATION: TNF-R1-Fc fusion protein of TNF-R1
      extracellular domain (AA 171-211) and huIgG1 (AA 99-120) with an
      overlapping amino acid (TNF-R1 AA 207 and huIgG1 AA 104)
```

```
<220> FEATURE:
<223> OTHER INFORMATION: Description of Artificial Sequence: fusion
      protein

<400> SEQUENCE: 71

Gly Phe Phe Leu Arg Glu Asn Glu Cys Val Ser Cys Ser Asn Cys Lys
 1               5                  10                  15

Lys Ser Leu Glu Cys Thr Lys Leu Cys Leu Pro Gln Ile Glu Asn Val
            20                  25                  30

Lys Gly Thr Glu Asp Lys Thr His Thr Cys Pro Pro Cys Pro Ala Pro
        35                  40                  45

Glu Leu Leu Gly Gly
    50

<210> SEQ ID NO 72
<211> LENGTH: 55
<212> TYPE: PRT
<213> ORGANISM: Artificial Sequence
<220> FEATURE:
<223> OTHER INFORMATION: TNF-R1-Fc fusion protein of TNF-R1
      extracellular domain (AA 171-211) and huIgG1 (AA 99-120) with an
      overlapping amino acid (TNF-R1 AA 211 and huIgG1 AA 106)
<220> FEATURE:
<223> OTHER INFORMATION: Description of Artificial Sequence: fusion
      protein

<400> SEQUENCE: 72

Gly Phe Phe Leu Arg Glu Asn Glu Cys Val Ser Cys Ser Asn Cys Lys
 1               5                  10                  15

Lys Ser Leu Glu Cys Thr Lys Leu Cys Leu Pro Gln Ile Glu Asn Val
            20                  25                  30

Lys Gly Thr Glu Asp Ser Gly Thr Thr His Thr Cys Pro Pro Cys Pro
        35                  40                  45

Ala Pro Glu Leu Leu Gly Gly
    50                  55

<210> SEQ ID NO 73
<211> LENGTH: 54
<212> TYPE: PRT
<213> ORGANISM: Artificial Sequence
<220> FEATURE:
<223> OTHER INFORMATION: TNF-R1-Fc fusion protein of TNF-R1
      extracellular domain (AA 171-211) and huIgG1 (AA 99-120) with an
      overlapping amino acid (TNF-R1 AA 210 and huIgG1 AA 106)
<220> FEATURE:
<223> OTHER INFORMATION: Description of Artificial Sequence: fusion
      protein

<400> SEQUENCE: 73

Gly Phe Phe Leu Arg Glu Asn Glu Cys Val Ser Cys Ser Asn Cys Lys
 1               5                  10                  15

Lys Ser Leu Glu Cys Thr Lys Leu Cys Leu Pro Gln Ile Glu Asn Val
            20                  25                  30

Lys Gly Thr Glu Asp Ser Gly Thr His Thr Cys Pro Pro Cys Pro Ala
        35                  40                  45

Pro Glu Leu Leu Gly Gly
    50

<210> SEQ ID NO 74
<211> LENGTH: 461
<212> TYPE: PRT
<213> ORGANISM: human
<220> FEATURE:
<223> OTHER INFORMATION: TNF-R2 >sp/P20333/TR1B_HUMAN necrosis factor
      receptor superfamily member 1B precursor (p80)
```

(TNF-R2) (p75) (CD120b) [contains: Tumor necrosis
factor binding protein 2 (TBPII)]

<400> SEQUENCE: 74

```
Met Ala Pro Val Ala Val Trp Ala Ala Leu Ala Val Gly Leu Glu Leu
 1               5                   10                  15

Trp Ala Ala His Ala Leu Pro Ala Gln Val Ala Phe Thr Pro Tyr
             20                  25                  30

Ala Pro Glu Pro Gly Ser Thr Cys Arg Leu Arg Glu Tyr Tyr Asp Gln
             35                  40                  45

Thr Ala Gln Met Cys Cys Ser Lys Cys Ser Pro Gly Gln His Ala Lys
     50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                 85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
        130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Asp His Ser Ser Gln Cys Ser Ser Gln
385                 390                 395                 400
```

Ala Ser Ser Thr Met Gly Asp Thr Asp Ser Ser Pro Ser Glu Ser Pro
            405                 410                 415

Lys Asp Glu Gln Val Pro Phe Ser Lys Glu Cys Ala Phe Arg Ser
        420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460

<210> SEQ ID NO 75
<211> LENGTH: 37
<212> TYPE: PRT
<213> ORGANISM: human
<220> FEATURE:
<223> OTHER INFORMATION: TNF-R2 extracellular domain (AA 221-257)

<400> SEQUENCE: 75

Ser Thr Arg Ser Gln His Thr Gln Pro Thr Pro Glu Pro Ser Thr Ala
1               5                   10                  15

Pro Ser Thr Ser Phe Leu Leu Pro Met Gly Pro Ser Pro Pro Ala Glu
            20                  25                  30

Gly Ser Thr Gly Asp
        35

<210> SEQ ID NO 76
<211> LENGTH: 53
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 252 and huIgG1 AA 99)
<220> FEATURE:
<223> OTHER INFORMATION: Description of Artificial Sequence: fusion
      protein

<400> SEQUENCE: 76

Ser Thr Arg Ser Gln His Thr Gln Pro Thr Pro Glu Pro Ser Thr Ala
1               5                   10                  15

Pro Ser Thr Ser Phe Leu Leu Pro Met Gly Pro Ser Pro Pro Ala Glu
            20                  25                  30

Pro Lys Ser Cys Asp Lys Thr His Thr Cys Pro Pro Cys Pro Ala Pro
        35                  40                  45

Glu Leu Leu Gly Gly
    50

<210> SEQ ID NO 77
<211> LENGTH: 50
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 250 and huIgG1 AA 100)
<220> FEATURE:
<223> OTHER INFORMATION: Description of Artificial Sequence: fusion
      protein

<400> SEQUENCE: 77

Ser Thr Arg Ser Gln His Thr Gln Pro Thr Pro Glu Pro Ser Thr Ala
1               5                   10                  15

Pro Ser Thr Ser Phe Leu Leu Pro Met Gly Pro Ser Pro Pro Lys Ser
            20                  25                  30

Cys Asp Lys Thr His Thr Cys Pro Pro Cys Pro Ala Pro Glu Leu Leu 35              40                  45
Gly Gly
    50

<210> SEQ ID NO 78
<211> LENGTH: 49
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 249 and huIgG1 AA 100)
<220> FEATURE:
<223> OTHER INFORMATION: Description of Artificial Sequence: fusion
      protein

<400> SEQUENCE: 78

Ser Thr Arg Ser Gln His Thr Gln Pro Thr Pro Glu Pro Ser Thr Ala
  1               5                  10                  15

Pro Ser Thr Ser Phe Leu Leu Pro Met Gly Pro Ser Pro Lys Ser Cys
                 20                  25                  30

Asp Lys Thr His Thr Cys Pro Pro Cys Pro Ala Pro Glu Leu Leu Gly
             35                  40                  45

Gly

<210> SEQ ID NO 79
<211> LENGTH: 52
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 254 and huIgG1 AA 102)
<220> FEATURE:
<223> OTHER INFORMATION: Description of Artificial Sequence: fusion
      protein

<400> SEQUENCE: 79

Ser Thr Arg Ser Gln His Thr Gln Pro Thr Pro Glu Pro Ser Thr Ala
  1               5                  10                  15

Pro Ser Thr Ser Phe Leu Leu Pro Met Gly Pro Ser Pro Pro Ala Glu
                 20                  25                  30

Gly Ser Cys Asp Lys Thr His Thr Cys Pro Pro Cys Pro Ala Pro Glu
             35                  40                  45

Leu Leu Gly Gly
    50

<210> SEQ ID NO 80
<211> LENGTH: 46
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 248 and huIgG1 AA 102)
<220> FEATURE:
<223> OTHER INFORMATION: Description of Artificial Sequence: fusion
      protein

<400> SEQUENCE: 80

Ser Thr Arg Ser Gln His Thr Gln Pro Thr Pro Glu Pro Ser Thr Ala
  1               5                  10                  15

Pro Ser Thr Ser Phe Leu Leu Pro Met Gly Pro Ser Cys Asp Lys Thr
                 20                  25                  30

His Thr Cys Pro Pro Cys Pro Ala Pro Glu Leu Leu Gly Gly

```
<210> SEQ ID NO 81
<211> LENGTH: 53
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 257 and huIgG1 AA 104)
<220> FEATURE:
<223> OTHER INFORMATION: Description of Artificial Sequence:  fusion
      protein

<400> SEQUENCE: 81

Ser Thr Arg Ser Gln His Thr Gln Pro Thr Pro Glu Pro Ser Thr Ala
  1               5                  10                  15

Pro Ser Thr Ser Phe Leu Leu Pro Met Gly Pro Ser Pro Pro Ala Glu
             20                  25                  30

Gly Ser Thr Gly Asp Lys Thr His Thr Cys Pro Pro Cys Pro Ala Pro
         35                  40                  45

Glu Leu Leu Gly Gly
     50

<210> SEQ ID NO 82
<211> LENGTH: 49
<212> TYPE: PRT
<213> ORGANISM: Artificial Sequence
<220> FEATURE:
<223> OTHER INFORMATION: TNF-R2-Fc fusion protein of TNF-R2
      extracellular domain (AA 221-257) and huIgG1 (AA 99-120) with an
      overlapping amino acid (TNF-R2 AA 255 and huIgG1 AA 106)
<220> FEATURE:
<223> OTHER INFORMATION: Description of Artificial Sequence:  fusion
      protein

<400> SEQUENCE: 82

Ser Thr Arg Ser Gln His Thr Gln Pro Thr Pro Glu Pro Ser Thr Ala
  1               5                  10                  15

Pro Ser Thr Ser Phe Leu Leu Pro Met Gly Pro Ser Pro Pro Ala Glu
             20                  25                  30

Gly Ser Thr His Thr Cys Pro Pro Cys Pro Ala Pro Glu Leu Leu Gly
         35                  40                  45

Gly
```

CD95-FC FUSION PROTEINS

The invention relates to fusion proteins comprising at least a biologically active polypeptide domain and a second domain selected from a constant immunoglobulin domain.

Fusion proteins comprising an immunoglobulin heavy and/or light chain dimer or an immunoglobulin heavy and/or light chain tetramer, in which an amino acid sequence of a ligand-binding partner which is a receptor, a carrier protein, a hormone, a growth factor or an enzyme, is substituted for the variable region of at least one immunoglobulin chain, are described in EP-A-0 526 452. A fusion protein comprising the extra cellular domain of the death receptor CD95 (APO-1; Fas) fused to an immunoglobulin Fc fragment is described in WO 95/27735. N-terminally truncated derivatives of the APO-1 molecule optionally fused to immunoglobulin Fc fragments are disclosed in EP-A-0 965 637. A fusion protein consisting of soluble IL-15Rα and Fc fragments is disclosed in WO 98/36768. A fusion protein consisting of an antagonist IL-15 mutant and an Fc IgG2a fragment is disclosed by Kim et al. (*J. Immunol.* 160 (1998), 5742-5748). These documents are incorporated herein by reference.

Although it has been shown that fusion proteins as described above have high biological activity in vitro and in vivo, there are concerns with regard to the immunogenic potential of such molecules since there is a fusion region between two protein domains of different origin comprising a non-naturally occurring amino sequence which may elicit an undesired immune response in an organism to which the fusion protein is administered.

WO 02/066514 describes artificial fusion proteins having a reduced immunogenicity compared to the parent non-modified molecule when exposed to a species in vivo. These proteins essentially consist of an immunoglobulin molecule or a fragment thereof covalently fused via its C-terminus to the N-terminus of a biologically active non-immunoglobulin molecule, preferably a polypeptide or protein or a biologically active fragment thereof. The molecules have amino acid sequences which are altered in one or more amino acid residue positions but, in principle, have the same biological activity as compared with the non-altered molecules. The changes are made in regions of the molecules which are identified as T-cell epitopes, which contribute to an immune reaction in a living host. A disadvantage of this procedure, however, is that not all epitopes, particularly not B-cell epitopes, can be reliably eliminated. Furthermore, the introduction of non-naturally occurring amino acid sequences can lead to the generation of neo-epitopes.

Thus, it was an object of the present invention to provide fusion proteins with at least two domains of different origin having a reduced immunogenic potential.

Thus, the present invention relates to a fusion protein comprising
(i) at least one first domain comprising a biologically active polypeptide and
(ii) a heterologous second domain comprising at least a portion of a constant immunoglobulin domain,
wherein there is at least one amino acid overlap between the first domain and the second domain in the fusion region.

The fusion protein may be a monomeric protein or a multimeric protein, e.g. a dimeric or tetrameric protein, which may be formed by multimerisation via the constant immunoglobulin domain.

According to the present invention, the design of a fusion protein comprises i) the selection of at least one first domain and a second domain which is heterologous to the first domain and ii) the selection of at least one terminal amino acid which is common to the first and the second domain, e.g. the last amino acid(s) of the first domain is (are) selected such that they are identical with the first amino acid(s) of the second domain. Preferably, the overlap has a length of one, two or three amino acids. Thus, a fusion protein is obtained which is free from a non-naturally occurring transition between the last amino acid of one domain and the first amino acid of another domain.

In an embodiment of the invention, the first domain(s) is (are) located at the N-terminus of the fusion protein, whereas the second domain is located at the C-terminus. Thus, in this embodiment, at least one carboxy terminal amino acid of a first domain overlaps with at least one amino terminal acid of the second domain.

In a further embodiment the second domain is located at the N-terminus of the fusion protein and the first domain(s) is (are) located at the C-terminus. Thus, in this embodiment, at least one carboxy terminal amino acid of the second domain overlaps with at least one amino terminal acid of a first domain.

In cases where the fusion protein comprises more than one, e.g. two or three, first domains, these domains are preferably located sequentially at the N-terminus or the C-terminus of the fusion protein and the second domain at the C-terminus or at the N-terminus, respectively. It should be noted that the first domains in such proteins may be the same or different. Transitions between individual first domains are preferably designed such that there is also at least one amino acid overlap (and thus not a non-naturally occurring transition between the last amino acid of one domain and the first amino acid of the other domain) between the individual first domains. Fusion proteins comprising multiple first domains are disclosed in WO 00/18932 which is incorporated herein by reference.

The first domain of the fusion protein comprises a biologically active polypeptide, i.e. a polypeptide which is capable of interacting with, e.g. binding to, a binding partner, e.g. another polypeptide, in its natural environment in a cell or an organism and which is preferably capable of exhibiting a pharmacological activity. The first domain is preferably a non-immunoglobulin polypeptide. The first domain may be a naturally occurring polypeptide or a variant thereof having desired, e.g. increased or reduced, biological activity or a fragment of a naturally occurring polypeptide or a variant thereof. The first domain is preferably selected from the ligand-binding domain of a receptor and a receptor-binding domain of a ligand. The terms "ligand" and "receptor" are understood in this context such that ligands are defined as proteins known to function to bind specifically to receptor molecules. The term "receptor" includes soluble or membrane-anchored receptor proteins having a hydrophobic transmembrane region or a phospholipid anchor. Further, the term "receptor" encompasses carrier proteins as well as hormones, cellular adhesive proteins, lectins, growth factors, enzymes, etc.

In a preferred embodiment of the invention the first domain is a ligand-binding receptor domain comprising the extracellular domain of a membrane-anchored receptor or a ligand-binding fragment thereof. The receptor is preferably selected from death receptors, growth factor receptors and cytokine receptors. More preferably, the receptor is selected from CD95 (APO-1; Fas), TRAIL receptors, TNF receptors, VEGF receptors, an interleukin receptor such as IL-15Rα. Most preferably the receptor is CD95, a TRAIL receptor, e.g. the TRAIL receptor-1, the TRAIL receptor-2, the TRAIL receptor-3 or the TRAIL receptors or a TNF receptor, e.g. the TNF receptor-1 or the TNF receptor-2.

In a further embodiment, the first domain is a receptor-binding ligand domain. The ligand is preferably selected from death ligands such as the CD95 ligand, TRAIL, TNF, e.g. TNF-α or TNF-β, growth factors, e.g. VEGF and cytokines, such as interferons or interleukins, e.g. IL-15 or variants thereof.

In a still further embodiment, the fusion protein comprises multiple first domains which may be the same or different. A preferred example of such a multiple fusion protein is a VEGF Trap fusion protein comprising the second extracellular domain of the VEGF receptor 1 (Flt-1) with the third domain of the VEGF receptor 2 (KDR/FIK-1) and an IgG constant region.

The first domain protein is preferably a mammalian protein, more preferably a human protein. For therapeutic purposes in particular, the use of human proteins is preferred.

The second domain of the fusion protein comprises at least a portion of a constant immunoglobulin domain, e.g. a constant heavy immunoglobulin domain or a constant light immunoglobulin domain. Preferably, the second domain comprises at least a portion of a constant heavy immunoglobulin domain. The constant heavy immunoglobulin domain is preferably an Fc fragment comprising the CH2 and CH3 domain and, optionally, at least a part of the hinge region. The immunoglobulin domain may be an IgG, IgM, IgD or IgE immunoglobulin domain or a modified immunoglobulin domain derived, therefrom. Preferably, the second domain comprises at least a portion of a constant IgG immunoglobulin domain. The IgG immunoglobulin domain may be selected from IgG1, IgG2, IgG3 of IgG4 domains or from modified domains such as are described in U.S. Pat. No. 5,925,734. The immunoglobulin domain may exhibit effector functions, particularly effector functions selected from ADCC and/or CDC. In some embodiments, however, modified immunoglobulin domains having modified, e.g. at least partially deleted, effector functions may be used.

Designing the fusion protein of the present invention comprises a selection of the terminal amino acid(s) of the first domain and of the second domain in order to create an at least one amino acid overlap between both domains. In order to achieve this goal it is usually necessary to delete one or several amino acids from a first and/or second domain and/or to add one or several amino acids from the naturally occurring adjacent domain to the first and/or second domain. For example, it may be necessary to provide a first domain having a deletion of preferably up to 10 and, more preferably, up to 6 amino acids, e.g. 1, 2, 3, 4, 5 or 6 amino acids from naturally occurring domain boundaries. On the other hand, it may be required to add preferably up to 10 and, more preferably, up to 6 amino acids, e.g. 1, 2, 3, 4, 5 or 6 amino acids from a naturally occurring adjacent domain to the first and/or second domain. When deleting and/or adding amino acids, however, one has to take care that the biological activity of the first domain and/or the second domain is not detrimentally affected.

The fusion protein of the invention may comprise an N-terminal signal sequence which allows secretion from a host cell after recombinant expression. The signal sequence may be a signal sequence which is homologous to the first domain of the fusion protein. Alternatively, the signal sequence may also be a heterologous signal sequence, e.g. the Igκ or the Igλ signal peptide sequence. In a different embodiment, the fusion protein is free from an N-terminal sequence, thus representing the mature form of the fusion protein.

The overlap between the first and the second domain or between two first domains has a length of preferably 1, 2 or 3 amino acids. More preferably the overlap has a length of one amino acid. Examples of overlapping amino acids are S, E, K, H, T, P and D.

The present invention is explained in detail below with regard to several specific preferred embodiments. It should be noted, however, that further fusion proteins of the invention may be manufactured by analogous means.

In a first preferred embodiment the first domain is the extracellular domain of human CD95. The extracellular domain of the fusion protein preferably comprises the amino acid sequence up to amino acid 170, 171, 172 or 173 of human CD95. Preferably, the extracellular domain of CD95 is fused with a human IgG Fc fragment, e.g. a human IgG1 Fc fragment. The amino acid sequence of the human CD95 molecule is shown in FIG. 1. The amino acid sequence of the human IgG1 chain constant domain is shown in FIG. 2. Especially preferred is the fusion protein comprising the amino acid sequence as shown in FIGS. 3A and 3B, wherein the overlapping amino acid sequence is S.

In a further especially preferred embodiment the first domain is the extracellular domain of a human TRAIL receptor, e.g. the human TRAIL receptor-1, the human TRAIL receptor-2, the human TRAIL receptor-3 and the human TRAIL receptor-4. The extracellular domain preferably comprises the amino acid sequence up to amino acid 232, 233, 234, 235, 236, 237, 238, 239 (TRAILR-1), 204, 205, 206, 207, 208, 209, 210 (TRAILR-2 long), 185, 186, 187, 188, 189, 190, 191 (TRAILR-2 long—without repeat), 179, 180, 181, 182, 183, 184 (TRAILR-2 short), 228, 229, 230, 231, 232, 233, 234, 235, 236, (TRAILR-3), 151, 152, 153, 154, 155, 156, 157, 158, 159, 160, 161 (TRAILR-3 without repeat) and 201, 202, 203, 204, 205, 206, 207, 208, 209, 210, 211 (TRAILR-4). Especially preferred is the human TRAIL receptor-2. The extracellular human TRAIL receptor domain may be fused with a human IgG-1 Fc fragment. The amino acid sequences of human TRAIL receptors are shown in FIG. 4 (TRAILR-1), FIG. 6 (TRAILR-2 long), FIG. 9 (TRAILR-2 short), FIG. 11 (TRAIL-3) and FIG. 14 (TRAILR-4). Specific examples of preferred fusion proteins comprise amino acid sequences as shown in FIGS. 5, 7, 8, 10, 12, 13 and 15.

In still a further preferred embodiment the fusion protein comprises a first domain which is the extracellular domain of a human TNF receptor, e.g. a human TNF receptor-1 or a human TNF receptor-2. The extracellular domain preferably comprises the amino acid sequence up to amino acid 203, 204, 205, 206, 207, 208, 209, 210, 211 (TNF-R1) or 248, 249, 250, 251, 252, 253, 254, 255, 256, 257 (TNF-R2). The extracellular domain of the human TNF receptor may be fused to a human IgG-1 Fc fragment. The amino acid sequence of human TNF receptors are shown in FIGS. 16 (TNF-R1) and 18 (TNF-R2). Specific examples of preferred fusion protein comprise amino acid sequences as shown in FIGS. 17 and 19.

A further aspect of the present invention relates to a nucleic acid molecule encoding a fusion protein as described above. The nucleic acid molecule may be a DNA molecule, e.g. a double-stranded or single-stranded DNA molecule, or an RNA molecule. The nucleic acid molecule may encode the fusion protein or a precursor thereof, e.g. a pro- or pre-pro-form of the fusion protein which may comprise a signal sequence or other heterologous amino acid portions for secretion or purification which are preferably located at the N- and/or C-terminus of the fusion protein. The heterologous amino acid portions may be linked to the first and/or second domain via a protease cleavage site, e.g. a Factor $X_a$, thrombin or IgA protease cleavage site.

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosal integration vector, etc. Examples of suitable expression control sequences and vectors are described for example by Sambrook et al. (1989) *Molecular Cloning, A Laboratory Manual*, Cold Spring Harbor Press, and Ausubel et al. (1989), *Current Protocols in Molecular Biology*, John Wiley & Sons.

Various expression vector/host cell systems may be used to express the nucleic acid sequences encoding the fusion proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells.

Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical composition comprising as an active agent at least one fusion protein or a nucleic acid molecule coding thereof as described above. In an especially preferred embodiment, the first domain is a soluble death receptor, e.g. the extracellular domain of a death receptor as described above for use in the prophylaxis and/or treatment of disorders associated with apoptosis. Most preferably, the first domain is the extracellular CD95 domain.

In this embodiment of the invention the composition may be used in the prophylaxis and/or treatment of disorders selected from autoimmune disorders, AIDS, heart disorders, e.g. myocardial infarction, graft-versus-host-disorders, transplant rejection, brain damage, e.g. stroke, spinal cord injuries, e.g. paraplegia, sepsis, hepatitis, disorders associated with inflammation, ischemic reperfusion injury and renal disorders. These disorders and further disorders which may be treated by administration of death receptor fusion proteins, particularly CD95 fusion proteins, are described in WO 95/27735, WO 99/50413, WO 01/41803, EP-A-0 965 637 and EP-A-0 992 243 which are herein incorporated by reference.

The fusion protein is administered to a subject in need thereof, particularly a human patient, in a sufficient dose for the treatment of the specific conditions by suitable means. For example, the fusion protein may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e.g. intraperitoneally, intramuscularly or intravenously or locally, e.g. intranasally, subcutaneously or intrathecally. Preferred is intravenous administration.

Especially preferred is a death ligand inhibitor, e.g. a soluble extracellular CD95 or TRAIL receptor domain fused to an Fc fragment.

The dose of the fusion protein administered will of course be dependent on the subject to be treated, on the subject's weight, the type and severity of the injury, the manner of administration and the judgement of the prescribing physician. For the administration of CD95 or TRAIL-R fusion proteins, a daily dose of 0.001 to 100 mg/kg is suitable.

Moreover, the invention relates to a method for manufacturing a fusion protein comprising
(i) at least one first domain comprising a biologically active protein fused to
(ii) a second domain comprising at least a portion of a constant immunoglobulin domain with reduced immunogenic potential, wherein the first domain is fused to the second domain with at least one amino acid overlap.

Still a further aspect of the present relates to a fusion protein comprising:
(i) at least one first domain comprising a biologically active polypeptide fused to
(ii) a heterologous second domain which is capable of oligomerising the fusion protein wherein there is at least one amino acid overlap between the first and the second domain in the fusion region.

Fusion proteins comprising heterologous second domains which are capable or oligomerising the fusion proteins in the absence of third proteins are described in WO 01/49866 and in WO 02/090553, for example, which are incorporated herein by reference. The presence of at least one amino acid overlap, e.g. one, two or three amino acids overlap, between the first and the second domain in the fusion proteins leads—as explained above—to fusion proteins with reduced immunogenic potential.

The first domain in this oligomerising fusion protein is defined as above. Preferably, the first domain is an extracellular domain of a membrane-anchored receptor, or a ligand-binding fragment thereof. Especially preferred is that the receptor is selected from CD95, a TRAIL receptor, particularly the TRAIL receptor-2 and a TNF receptor, particularly the TNF receptor-2. Alternatively, the first domain may be a receptor-binding ligand domain, wherein the ligand is preferably selected from CD95 ligand, TRAIL and TNF. Specific examples of preferred first domains are as described above.

The second domain of the fusion protein comprises an oligomerising portion of a protein. Preferably, the second domain is capable of di- tri- tetra- or pentamerising the fusion protein. In this context, particular reference is made to the disclosure of WO 01/49866 and WO 02/090553, which are herein incorporated by reference. Preferred examples of second domains are C1q, MBP (Mannose Binding Protein), SP-A (Lung Surfactant Protein-A), SP-D (Lung Surfactant Protein-D), BC (Bovine Serum Conglutinine), CL43 (Bovine Collectine-43), ACRP-30 (a protein from the C1q family) and COMP (Cartilage Oligomeric Matrix Protein) or the collagen domain of EDA or a functionally active derivative thereof. Especially preferred are portions of ACRP-30, particularly of the human ACRP-30 protein, e.g. amino acids 18 to 108, or 18 to 110 or of COMP.

As described above, the first domain(s) of the fusion protein may be located at the N- or C-terminus and the second domain at the C- or N-terminus. Further, both the first and the second domains are preferably from the same species, more preferably of human origin. Furthermore, the features relating to preferred embodiments of the fusion proteins based on immunoglobulins also apply to the oligomerising fusion proteins.

The reduced immunogenic potential of the fusion protein results from the lack of non-naturally occurring transitions between the first and the second domain in the fusion proteins, which in turn leads to a decreased potential for the formation of neo-epitopes resulting from the fusion between two heterologous polypeptides.

The present invention is illustrated further by the following Figures and Examples.

FIGURE LEGEND

FIG. 1: the amino acid sequence of the human CD95 (APO-1; Fas) protein (SEQ ID NO: 13);

FIG. 2: the amino acid sequence of the human IgG-1 chain C-region (SEQ ID NO: 14);

FIGS. 3A and 3B: a preferred example of a CD95-Fc IgG1 fusion protein with an overlapping amino acid (SEQ ID NOs: 15-18);

FIG. 4: the amino acid sequence of the human TRAIL receptor-1 (SEQ ID NO: 19);

FIG. 5: preferred examples of TRAILR-1 Fc IgG1 fusion proteins with overlapping amino acids (SEQ ID NO: 20-24);

FIG. 6: the amino acid sequence of human TRAIL receptor-2 (long form) (SEQ ID NO: 25);

FIG. 7: preferred examples of TRAILR-2 (long) Fc IgG1 fusion proteins with overlapping amino acids, including a repeat sequence (SEQ ID NO: 26-32);

FIG. 8: preferred examples of TRAILR-2 (long form) Fc fusion proteins with overlapping amino acids (without repeat sequence) (SEQ ID NO: 33-38);

FIG. 9: the amino acid sequence of human TRAILR-2 (short form) (SEQ ID NO: 39);

FIG. 10: preferred examples of TRAILR-2 (short) Fc IgG1 fusion proteins with overlapping amino acids (SEQ ID NO: 40-44);

FIG. 11: the amino acid sequence of human TRAIL receptor R-3 (SEQ ID NO: 45);

FIG. 12: preferred examples of TRAILR-3 Fc IgG1 fusion proteins with overlapping amino acids (repeats included) (SEQ ID NO: 46-52);

FIG. 13: preferred examples of TRAILR-3 Fc IgG1 fusion proteins with overlapping amino acids (repeats not included) (SEQ ID NO: 53-58);

FIG. 14: the amino acid sequence of human TRAIL receptor-4 (SEQ ID NO: 59);

FIG. 15: preferred examples of TRAILR-4 Fc IgG1 fusion proteins with overlapping amino acids (SEQ ID NO: 60-64);

FIG. 16: the amino acid sequence of human tumor necrosis factor receptor-1 (SEQ ID NO: 65);

FIG. 17: preferred examples of TNFR-1 Fc IgG1 fusion proteins with overlapping amino acids (SEQ ID NO: 66-73);

FIG. 18: the amino acid sequence of human tumor necrosis factor receptor-2 (SEQ ID NO: 74);

FIG. 19: preferred examples of TNF-R2 Fc IgG1 fusion proteins with overlapping amino acids (SEQ ID NO: 75-82).

EXAMPLE 1

Fusion Protein Consisting of the Human CD95 Extracellular Domain and the Human IgG1 Fc Domain with Overlapping Amino Acids Human CD95 Extracellular Domain Bases 221-736 of Human CD95 (Genbank Acc. No. X63717). Utilized Sequence from Oehm, A., "Purification and Molecular Cloning of the APO-1 Cell Surface Antigen, a Member of the Tumour Necrosis Factor/Nerve Growth Factor Receptor Superfamily," Journal of Biological Chemistry Vol. 267, No. 15, pp. 10709-10715, 1992. cDNA was created from total RNA isolated from Peripheral Blood Lymphocytes (PBL) from donor blood by RT-PCR using Oligo dT primer. PCRs were used to amplify the cDNA of the extracellular domain of CD95 by including a restriction Hind III Site and a Kozak Sequence at the 5' of the Extracellular domain and at the 3' a BgI II site (termination of the extracellular domain). PCR primers for the amplification of CD95 cDNA with Taq polymerase:

```
Sense huCD95-Hind III:
                                     (SEQ ID NO: 1)
TATA AAGCTT GCC ACC ATG CTG GGC ATC TG Antisense huCD95-Bgl II:
                                     (SEQ ID NO: 2)
TATA AGATCT GGA TCC TTC CTC TTT GC
```

Human IgG1 Fc Domain

Sequence: 2050-2745 bp. Sequence used from, Ellison, J., "The nucleotide sequence of human immunoglobulin C gene", Nucleic Acid Research, Volume 10 Number 13, 1982. cDNA was created from total RNA isolated from Peripheral Blood Lymphocytes (PBL) from donor blood by RT-PCR using Oligo dT primer. A PCR was used to amplify the cDNA of human IgG1 Fc (partial hinge-CH3) by including a restriction BgI II site at the 5' of the primer and at the 3' primer after the stop codon, an Xho I site.

PCR primers for the amplification of IgG1 Fc cDNA with Taq polymerase:

```
Sense huIgG1Fc-BgIII:
                                     (SEQ ID NO: 3)
TATA AGATCT TGT GAC AAA ACT CAC ACA TG Antisense huIgG1Fc-XhoI:
                                     (SEQ ID NO: 4)
TATA CTCGAG TCA TTT ACC CGG AGA CAG GG
```

Cloning Procedure:

Following amplification the IgG1 Fc PCR product was digested with BgI II and Xho I. The CD95 PCR product was digested with Hind III and BgI II and pcDNA3.1 (with CMV promoter) with Hind III and Xho I. The products were purified via gel extraction (Qiagen Kit).

The huIgG1 Fc and CD95 fragments were ligated with T4 ligase into pcDNA3.1. After transfection of One Shot Top 10 chemically competent cells (*E. coli*) from Invitrogen Ordering # C4040-10 and amplification, a plasmid preparation was performed with Qiagen Plasmid Prep Kit.

A three point ligation was performed by digesting pcDNA3.1 with HindIII and XhoI, CD95EC with HindIII and BgIII, and huIgG1 Fc with BgIII and XhoI. The presence of the CD95-huIgG1 Fc insert in pcDNA3.1 was verified by sequencing and restriction enzyme analysis. The vector containing insert was digested with HindIII and XbaI and the insert was ligated into pcDNA3.1 containing the EF-1 promoter.

The Kozak sequence of the original CD95-Fc construct was changed from GCCACCATGC to GCCGCCACCATGG by amplification of the whole CD95-Fc product with the primers SEQ ID 5 and SEQ ID 6.

Primers for Changing the Kozak Sequence from GCCACCATGC to GCCGCCACCATGG:

```
ShuCD95EC_altKozak
                                     (SEQ ID NO. 5)
TATA AAGCTT GCC GCC ACC ATG GTG GGC ATC AS698 huIgG1Fc-Xho1
                                     (SEQ ID NO: 6)
TATA CTCGAG TCA TTT ACC CGG AGA CAG GG
```

Cloning Procedure:

The PCR product was cloned in pcDNA3.1/V5 His Topo vector from Invitrogen (Ordering # K4800-01), digested with Hind III and Xba I as well as pcDNA3.1 containing the pEF promoter and ligated with T4 Ligase.

Expression and Isolation

The construct encoding the final product was transfected into cell lines suitable for protein expression. Transfection can be performed by any standard method know to those skilled in the art. Examples include electroporation, liposomal mediated transfer, calcium phosphate transfection. Cell lines suitable for the expression include 293T cells, COS-1, COS-7 and CHO cells. Other cell lines may be used.

In this example, 293T cells were transiently transfected by the calcium phosphate method. Alternatively, CHO cells were transfected utilizing FuGene6 and stable clones were selected.

The desired protein can be purified from the cell culture medium by chromatographic methods. Methods include but are not limited to affinity chromatography on protein-G or protein-A columns, ion-exchange chromatography, hydrophobic interaction chromatography, size exclusion chromatography or a combination of these methods.

In the example the supernatant was purified on IgG columns (Amersham Pharmacia) according to the manufacturers instructions, leading to a highly purified product in a single step.

EXAMPLE 2

Fusion Protein Consisting of the TRAIL Receptor-2 and the Human IgG1 Fc Domain with Overlapping Amino Acids Human IgG1 Fc Domain:

Sequence used from, Ellison, J., "The nucleotide sequence of human immunoglobulin C gene", Nucleic Acid Research, Volume 10 Number 13, 1982. cDNA was created from total RNA isolated from Peripheral Blood Lymphocytes (PBL) from donor blood by RT-PCR using Oligo dT primer. A PCR was used to amplify the cDNA of human IgG1 Fc (partial hinge-CH3) with an overlapping sequence to TRAILR2 at the 5' end and at the 3' end after the stop codon an EcoRI site.

```
I. Primer: Sense_huIgG1
                                         (SEQ ID NO: 7)
cca ggg act cct gcc TCT TGT GAC AAA ACT CAC ACA TG
(Capital letters => part of huIgG1)

II. Primer: Antisense_ERIhuIgG1
                                         (SEQ ID NO: 8)
TATA gaa ttc tca ttt acc cgg aga cag gg
```

TRAILR2:

Utilized Sequence from Walczak H., "TRAIL-R2: a novel apoptosis-mediating receptor for TRAIL" The EMBO Journal Vol. 16, No. 17, pp. 5386-5397, 1997. (Accession number DDBJ/EMBLUGenBank: AF016849) cDNA was created from total RNA isolated from Peripheral Blood Lymphocytes (PBL) from donor blood by RT-PCR using an Oligo dT primer. A PCR was used to amplify the cDNA of TRAILR2 domain by including a restriction site Hind III and a Kozak Sequence at the 5' end and at the 3' end an overlapping sequence to human IgG1.

```
III. Primer: Sense_HIII_TRAILR2
                                         (SEQ ID NO: 9)
TATA aag ctt gcc gcc acc atg gaa caa cgg gga cag
aac IV. Primer: Antisense_TRAILR2
                                         (SEQ ID NO: 10)
gtg agt ttt gtc aca aga GGC AGG AGT CCC TGG
(Capital letters => part huTRAIL-R2, in reverse)
```

Cloning Procedure:

Following the amplification a gel extraction was performed to isolate the modified inserts. Then a third PCR utilizing both fragments was performed. Due to the overlap of both fragments and the primers at the end, this PCR joins in one product. Afterwards the product was digested with Hind III and EcoR I and ligated in a suitable expression vector, e.g. pcDNA3.1 (Invitrogen).

```
III. Primer: Sense_HIII_TRAILR2
                                         (SEQ ID NO: 11)
TATA aag ctt gcc gcc acc atg gaa caa cgg gga cag
aac II. Primer: Antisense_ERIhuIgG1
                                         (SEQ ID NO: 12)
TATA gaa ttc tca ttt acc cgg aga cag gg
```

Expression

The construct was cloned and expressed in suitable host cells as described in Example 1.

EXAMPLE 3

Use of a CD95-Fc Construct for the Regeneration and Functional Recovery after Spinal Cord Injury The CD95-Fc construct with overlapping amino acids as described in Example 1 was used for the treatment of spinal cord-injury in a mouse model as described by Demjen et al., *Nat. Med.* (Mar. 7, 2004). It was found that administration of the construct promotes regeneration and functional recovery after spinal cord injury.

EXAMPLE 4

Use of CD95-Fc Construct for the Attenuation of Brain Damage in Stroke

The CD95-Fc construct with overlapping amino acids was investigated for its influence on primary ischemic death and secondary inflammatory injury in a mouse model as described by Martin-Villalba et al. (*Cell Death Differ.* 8 (2001), 679-686). It was found that administration of the CD95-Fc construct resulted in a significant decrease in both infarct volumes and mortality.

The invention claimed is:

1. A fusion protein comprising
   (i) at least one first domain comprising a ligand binding domain of the CD95 receptor fused to
   (ii) a heterologous second domain comprising at least a portion of a constant immunoglobulin domain, wherein the fusion protein comprises the amino acid sequence of SEQ ID NO: 18.

2. The fusion protein of claim 1, wherein the second domain is an Fc fragment of a constant heavy immunoglobulin domain comprising the CH2 and CH3 domain.

3. The fusion protein of claim 1, further comprising an N-terminal signal sequence.

4. A pharmaceutical composition comprising as an active agent the fusion protein of claim 1.

5. A fusion protein comprising the amino acid sequence of SEQ ID NO: 15.

6. An isolated nucleic acid molecule encoding the fusion protein of claim 1.

7. The nucleic acid molecule of claim 6 which is operatively linked to an expression control sequence.

8. A vector comprising the nucleic acid molecule of claim 6.

9. An isolated cell transformed or transfected with the nucleic acid molecule of claim 6.

10. The cell of claim 9 which is a prokaryotic cell.

11. The cell of claim 9 which is a eukaryotic cell.

12. The cell of claim 9 which is a mammalian cell.

13. The cell of claim 9 which is a human cell.

14. A composition comprising the nucleic acid molecule of claim 6 and a pharmaceutically acceptable carrier.

* * * * *